(12) United States Patent
Egrise et al.

(10) Patent No.: US 8,337,827 B2
(45) Date of Patent: Dec. 25, 2012

(54) METHOD FOR OSTEOGENIC DIFFERENTIATION OF BONE MARROW STEM CELLS (BMSC) AND USES THEREOF

(75) Inventors: Dominique Egrise, Beersel (BE);
Valerie Gangji, Rhode-Saint Genese (BE); Jean-Philippe Hauzeur, Brussels (BE); Micheline Lambermont, Waterloo (BE); Michel Toungouz, Brussels (BE)

(73) Assignee: Universite Libre de Bruxelies, Brussels (BE)

( * ) Notice: Subject to any disclaimer, the term of this patent is extended or adjusted under 35 U.S.C. 154(b) by 1056 days.

(21) Appl. No.: 12/278,557

(22) PCT Filed: Feb. 16, 2007

(86) PCT No.: PCT/EP2007/001360
§ 371 (c)(1),
(2), (4) Date: Sep. 12, 2008

(87) PCT Pub. No.: WO2007/093431
PCT Pub. Date: Aug. 23, 2007

(65) Prior Publication Data
US 2009/0081169 A1    Mar. 26, 2009

(30) Foreign Application Priority Data
Feb. 16, 2006  (WO) ................. PCT/EP2006/001427

(51) Int. Cl.
*A61K 35/00* (2006.01)
*A01N 63/00* (2006.01)
(52) U.S. Cl. ..................................... 424/93.1; 424/93.7
(58) Field of Classification Search ................. 424/93.1, 424/93.7
See application file for complete search history.

(56) References Cited

U.S. PATENT DOCUMENTS
5,736,396 A    4/1998 Bruder et al.

FOREIGN PATENT DOCUMENTS
WO    WO 98/33515    8/1998
WO    WO 03/004605    1/2003
WO    WO 2004/007697    1/2004

OTHER PUBLICATIONS

Quirici et al (British Journal of Haematology, 115: 186-194, 2001).*
Gangji et al (J Bone Joint Surg Am, 86-A (6): 1153-60, 2004).*
Guillotin et al (Cell Physiol and Biochemistry, 14: 325-332, 2004).*
Zannetino et al (J Cell Biochem, 89(1): 56-66, 2003).*
Wulling et al, (Hum Pathol, 34: 983-993, 2003).*
Dominici, et al. "Minimal Criteria for Defining Multipotent Mesenchymal Stromal Cells. The International Society for Cellular Therapy Position Statement." *Cytotherapy*, vol. 8, No. 4, pp. 315-317, 2006.
Lisignoli, et al. "Basic Fibroblast Growth Factor Enhances In Vitro Mineralization of Rat Bone Marrow Stromal Cells Grown on non-woven Hyaluronic Acid Based Polymer Scaffold," *Biomaterials*, vol. 22, pp. 2095-2105, 2001.
Aubin, et al. "Osteoblast and Chondroblast Differentiation," *Bone*, vol. 17, No. 2, Supplement, pp. 77S-83S, Aug. 1995.
Deans, et al. "Mesenchymal Stem Cells: Biology and Potential Clinical Uses," *Experimental Hematology*, vol. 28, No. 8, pp. 875-884, Aug. 2000.
Gangji, et al. "Treatment of Osteonecrosis of the Femoral Head with Implantation of Autologous Bone-Marrow Cells," *The Journal of Bone and Joint Surgery*, vol. 87, Suppl. 1, No. Pt. 1, pp. 106-112, Mar. 2005.
Kobayashi, et al. "Motility and Growth of Human Bone-Marrow Mesenchymal Stem Cells During ex vivo Expansion in Autologous Serum," *The Journal of Bone and Joint Surgery, British Volume*, vol. 87, No. 10, pp. 1426-1433, Oct. 2005.
Lin, et al. "Using Human Plasma Supplemented Medium to Cultivate Human Bone Marrow-Derived Mesenchymal Stem Cell and Evaluation of Its Multiple-Lineage Potential," *Transplantation Proceedings*, vol. 37, No. 10, pp. 4504-4505, Dec. 2005.
Sotiropoulou, et al. "Characterization of the Optimal Culture Conditions for Clinical Scale Production of Human Mesenchymal Stem Cells," *Stem Cells*, vol. 24, No. 2, pp. 462-471, Feb. 2006.
Stewart, et al. "STRO-1, HOP-26 (CD63), CD49a and SB-10 (CD166) as Markers of Primitive Human Marrow Stromal Cells and Their More Differentiated Progeny: A Comparative Investigation in vitro," *Cell and Tissue Research*, vol. 313, pp. 281-290, 2003.
Takagi, et al. "In vitro Proliferation of Human Bone Marrow Mesenchymal Stem Cells Employing Donor Serum and Basic Fibroblast Growth Factor," *Cytotechnology*, vol. 43, No. 1-3, pp. 89-96, 2003.
International Search Report dated Jul. 4, 2007.

* cited by examiner

*Primary Examiner* — Gerald Leffers, Jr.
*Assistant Examiner* — Magdalene Sgagias
(74) *Attorney, Agent, or Firm* — Knobbe, Martens, Olson & Bear, LLP

(57) ABSTRACT

Methods for obtaining osteoprogenitors, osteoblasts or osteoblast phenotype cells, as well as cell populations including such cells, from human bone marrow stem cells in vitro or ex vivo are disclosed. Bone marrow stem cells are contacted with human serum or plasma and a growth factor or a biologically active variant or derivative thereof. In addition, osteoprogenitor, osteoblast or osteoblast phenotype cell types and cell populations are provided. The cell populations may include additional cell types, such as endothelial cells or progenitors. The osteoprogenitors, osteoblasts or osteoblast phenotype cells may be used in therapy, particularly bone therapy.

16 Claims, 2 Drawing Sheets

A)

B)

METHOD FOR OSTEOGENIC DIFFERENTIATION OF BONE MARROW STEM CELLS (BMSC) AND USES THEREOF

Cross-Reference to Related Applications

This application is the U.S. National Phase under 35 U.S.C. §371 of International Application PCT/EP2007/001360, filed Feb. 16, 2007, which claims priority to PCT/EP2006/001427, filed Feb. 16, 2006.

FIELD OF THE INVENTION

In an aspect, the invention relates to in vitro or ex vivo methods for osteogenic, and preferably at least in part also endothelial, differentiation of bone marrow stem cells (BMSC), and to applications of so differentiated cells. In a further aspect, the invention relates to particular types and populations of cells displaying characteristics akin to but new over previously disclosed osteoprogenitors and osteoblasts. In related aspects, the invention provides uses, in particular in the field of therapy, preferably bone therapy, of the above methods, cells and cell populations obtainable using the methods, and of the cell types and cell populations specifically described herein.

BACKGROUND TO THE INVENTION

The feasibility of allogeneic bone marrow transplantation was demonstrated in children with severe osteogenesis imperfecta (Horwitz et al. 1999. Nat Med 5(3): 309-13). In that study, functional marrow-derived mesenchymal cells engrafted and contributed to the formation of new dense bone, indicating that the transplanted cells differentiated to bone-producing osteoblasts. Autologous bone marrow transplantation was also reported in a patient suffering from osteonecrosis of the humeral head (Hernigou et al. 1997. J Bone Joint Surg Am 79:1726-1730). Therefore, transplantation of stem cells capable of undergoing osteogenic differentiation or of cells that are committed towards osteogenic differentiation may be a promising avenue for the treatment of bone-related diseases, in particular when the treatment requires production of new bone.

Hence, there exists a great need for efficient techniques which provide sufficient quantities of cells, in particular autologous cells, suitable for transplantation as a remedy for bone-related disorders.

While undifferentiated bone marrow stem cells may be transplanted, these cells are not yet committed to an osteogenic lineage and therefore a considerable proportion of the transplanted stem cells may not eventually contribute to formation of bone tissue. In addition, it has been demonstrated (Banfi et al. 2000. Exp Hematol 28: 707-15) that in vitro culturing of bone marrow stem cells decreases their proliferation potential as well as their capability to undergo differentiation when treated with growth factors like FGF-2. For example, in that study, bone forming efficiency of in vitro cultured bone marrow stem cells was decreased 36 times already at first passage, compared to freshly isolated bone marrow. Hence, in vitro expansion of bone marrow stem cells may decrease their efficiency as a source of bone-forming osteoblasts upon transplantation.

Martin et al. (Endocrinology 138: 4456-4462, 1997) demonstrates that in vitro culturing of bone marrow stem cells in the presence of fibroblast growth factor type 2 (FGF-2), in combination with foetal calf serum (FCS) components, keeps the cells in an immature state (less alkaline phosphatase and fibroblast-like morphology), albeit the cells are competent to undergo osteogenic differentiation in vitro under specific osteogenic culture conditions. However, differentiation of such immature cells into bone-producing osteoblasts in vivo still depends on the provision of the appropriate signals upon transplantation. Hence, although such cells might be capable of osteogenic differentiation in vitro, a considerable proportion thereof may still not become osteoblasts in vivo. Also, Chaudhary et al. (Bone 34: 402-11, 2004) shows that human bone marrow stem cells treated with FGF-2 do not demonstrate any osteogenic phenotype (no alkaline phosphatase expression) and in fact have dystrophic morphology. Similarly, Kalajzic et al. (J Cell Biochem 88: 1168-76, 2003) demonstrates that FGF-2 inhibits osteogenic differentiation.

In addition, preparation of materials for use in human therapy should avoid the use of non-human animal components, such as serum components (e.g., FCS) in the culture media. However, as shown by Kuznetsov et al. (Transplantation 70: 1780-1787, 2000), the use of homologous or autologous human sera greatly diminishes the ability of human bone marrow stem cells to form colonies and expand in vitro, and to form bone in vivo. Hence, Kuznetsov et al. suggest that the use of FCS is prerequisite for efficient expansion of bone marrow stem cells and for their capacity to form bone.

Takagi et al. 2003 (Cytotechnology 43: 89-96) incubated human bone marrow aspirates in donor serum supplemented with FGF-2, under specific conditions. The cell population so-obtained by Takagi et al. 2003 only showed chondrogenic differentiation potential and was thus contemplated by the authors for use in the regeneration of cartilage.

Kobayashi et al. 2005 (J Bone Joint Surg Br 87: 1426-3) describes particular conditions for isolation and maintenance of human BMSC in autologous donor serum, concluding that these conditions may provide for sufficient ex vivo expansion of human BMSC, while preserving their multi-differentiation potential. FGF-2 is employed by Kobayashi et al. 2005 in secondary culture to promote further BMSC expansion without differentiation. These authors do not disclose conditions which would cause their cells to progress towards osteoprogenitors or osteoblast phenotype cells.

Lin et al. 2005 (Transplant Proc 37: 4504-5) reported prolonged expansion of multi-potential human BMSC in autologous donor serum. Addition of FGF-2 and EGF to the cells under certain conditions did not influence cell proliferation and did not cause progression of the cells towards osteogenic fate.

In order to provide for maximum bone formation, it would be desired to transplant cells which already show an osteoblastic phenotype, since such cells are essentially the only ones with a demonstrated bone-forming activity. However, in vitro differentiation of bone marrow stem cells into osteoblasts involves culturing in osteogenic medium (Jaiswal et al. 1997. J Cell Biochem 64: 295-312) and may lead to decreased proliferation of such cells in vitro. Moreover, the use of osteogenic medium involves addition of further components to the cells, which may increase the risk of contamination of the cell culture.

Hence, there exists a need in the art for a simple and reliable method to produce osteoprogenitors, osteoblasts or osteoblastic phenotype cells from human adult stem cells, in particular human bone marrow stem cells, in vitro while maintaining high expansion capacity of the cells, ensuring autologous conditions and minimising the number of components involved in culturing of the cells.

There also exists need in the art for osteoprogenitor or osteoblastic cells having specific useful characteristics, e.g., in the context of bone therapy, and for cell populations comprising such cells.

SUMMARY OF THE INVENTION

The present invention addresses the above and other problems of the prior art.

In particular, the inventors realised that adult stem cells, in particular bone marrow stem cells (BMSC), advantageously of human origin, can be readily expanded ex vivo and directed towards useful osteoprogenitor or osteoblast phenotypes, and useful cell populations comprising such and other phenotypes, using herein disclosed culture conditions.

Accordingly, in an aspect, the invention relates to a method for obtaining osteoprogenitors, osteoblasts or osteoblast phenotype cells from human bone marrow stem cells in vitro or ex vivo, comprising contacting the bone marrow stem cells with human plasma or serum and a growth factor or a biologically active variant or derivative thereof.

The inventors observed that methods of the invention can differentiate a substantial fraction, e.g., a majority, of exposed stem cells toward the osteoprogenitor or osteoblast phenotypes. Consequently, in an aspect the methods of the invention can be employed for obtaining osteoprogenitors, osteoblasts or osteoblast phenotype cells per se.

Nevertheless, it can be appreciated that the methods of the invention generally produce cell populations comprising osteoprogenitors, osteoblasts or osteoblast phenotype cells, usually populations comprising a substantial portion, e.g., a majority, of such cells. The inventors also realised that cell populations resulting from the method may comprise further cell types, at least some of which can augment the useful characteristics of the osteoprogenitor or osteoblast phenotype cells present in such populations, in particular in the context of bone therapy. For example, in an embodiment a cell population resulting from the methods of the invention may also comprise endothelial cells or endothelial progenitors.

Accordingly, in an aspect, the invention relates to a method for obtaining a cell population comprising osteoprogenitors, osteoblasts or osteoblast phenotype cells from human bone marrow stem cells in vitro or ex vivo, comprising contacting the bone marrow stem cells with human plasma or serum and a growth factor or a biologically active variant or derivative thereof.

As shown by experimental evidence, the method of the invention may provide for expansion of the bone marrow stem cells between 40,000 to 710,000 times over three weeks, more particularly twenty one days. Such high degree of expansion is surprising in view of prior art teaching that the use of human serum markedly diminishes expansion of human bone marrow stem cells (Kuznetsov et al. 2000). Hence, the present invention allows for generation of a high number of cells for the purposes of transplantation. This advantageously decreases the size of the bone marrow sample which needs to be drawn from a subject in order to provide for the stem cells. In addition, the invention allows for shortening the time when the differentiated cells can be transplanted into a patient, thus resulting in faster therapy.

In a preferred embodiment, the method uses fibroblast growth factor and, in particular, FGF-b, i.e., FGF-2. It is surprising, in view of the prior art teaching that FGF-2 causes a more immature phenotype of bone marrow stem cells (Martin et al. 1997, Kalajzic et al. 2003), that the use of FGF-2 in combination with human plasma or serum components stimulates differentiation of bone marrow stem cells to attain the phenotypic characteristics of osteoprogenitors, osteoblasts or osteoblast phenotype cells.

Hence, the present method provides for unexpected advantageous effect—high expansion and osteoblast phenotype—by combining elements which have been known in prior art to provide for opposite effects when used separately. Even more strikingly, the prior art taught that in vitro differentiation into osteoblasts requires osteogenic medium, containing components such as dexamethasone, ascorbic acid phosphate and beta-glycerolphosphate. The present invention surprisingly shows that such components are not needed for obtaining osteoprogenitors, osteoblasts or osteoblast phenotype cells. Hence, the number of components in a medium may be advantageously decreased, resulting in less chances of error or contamination, or carryover of such components upon transplantation.

In further preferred embodiments, the method uses human plasma or serum which is autologous to the bone marrow stem cells and/or does not include any non-human animal material (such as serum components) in the culture of bone marrow stem cells. This makes the method particularly advantageous for use in human therapy, e.g., by decreasing the risk of rejection of the obtained cells and/or by decreasing the risk of contamination with pathogens.

Additional preferred embodiments of the method define other features, e.g., without limitation, incubation times, passages, component quantities, etc., which alone or in combination further delimit the method from prior art and underlie the provision of cells and cell populations of advantageous characteristics, e.g., of superiority in bone transplantation.

The inventors realised that osteoprogenitors, osteoblasts or osteoblast phenotype cells, as well as cell populations, obtainable using the methods of the invention show exemplary advantages over the prior art. Firstly, at least during the ex vivo culturing, the said cells show a fast proliferation rate, with an estimated doubling time of approximately 2 days. Hence, sufficient numbers of the cells can be generated within comparably short time, which advantageously limits the patient treatment periods. Secondly, the cells show a relatively fast rate of substrate mineralization, which allows for enhanced bone-formation upon transplantation of the cells into patients. Third, the cells display little or substantially no propensity for differentiation towards other mesenchymal phenotypes, in particular towards adipocytes or chondrocytes. This can advantageously limit the formation of tissue other than bone when the cells are transplanted.

Accordingly, in other aspects, the invention provides for osteoprogenitors, osteoblasts or osteoblast phenotype cells, as well as for cell populations and cultures comprising such, which are obtainable or directly obtained using the methods of the invention, and also for therapeutic uses thereof in bone-related disorders and corresponding pharmaceutical formulations comprising such.

In a further development of the invention, the inventors analysed in detail the cells and cell populations obtained carrying out the methods of the invention, in order to define new osteogenic cell types and new cell populations comprising such, that may offer particular superiority in therapy, especially in bone transplantation therapy. Consequently, the invention also contemplates such new cell types, populations comprising such, as well as uses thereof, especially in bone therapy.

Accordingly, in an aspect, the invention provides osteoprogenitor, osteoblast or osteoblast phenotype cells (herein, "OOP-1 cells") characterised in that they co-express (1) at least one osteoblast marker chosen from alkaline phosphatase (ALP), more specifically ALP of the bone-liver-kidney type, procollagen type 1 amino-terminal propeptide (P1NP) and bone sialoprotein (BSP) with (2) at least one stem cell/immature osteoprogenitor marker chosen from CD63 (by means of example, as recognised by antibody HOP-26; see Zannettino et al. 2003. J Cell Biochem. 89: 56-66) and CD166. Under (1): in a preferred embodiment, the said OOP-1 cells may express at least ALP; in further preferred embodiments, the said OOP-1 cells may express at least two markers chosen from ALP, P1NP and BSP, e.g., at least ALP and P1NP, at least ALP and BSP or at least P1NP and BSP; in a yet further preferred embodiment, the said OOP-1 cells may express at least all three of ALP, BSP and P1NP. Under (2): in a preferred embodiment, the said OOP-1 cells may express at least CD63; in another preferred embodiment, the said OOP-1 cells may express at least CD166; in a further preferred embodiment, the said OOP-1 cells may express at least CD63 and CD166.

To the inventors' best knowledge the prior art only observed CD63 and/or CD166 in stem cells/immature osteoprogenitors when ALP, P1NP and BSP were negative. Such CD63 and/or CD 166 positive cells of prior art showed multi-potency and could differentiate to chondrocytes, adipocytes as well as osteoblasts. Hence, the concomitant presence of at least one of ALP, P1NP or BSP with CD63 and/or CD166 marks the osteoprogenitor or osteoblast phenotype cells of the invention (OOP-1 cells) as a new, previously undisclosed cell type. Moreover, this new cell type displays at least some of advantageous properties such as high proliferation rate, high mineralization rate and substantially absent propensity towards chondrocytic and adipocytic differentiation, which are particularly useful, e.g., in bone therapeutic context.

In a preferred embodiment, the said osteoprogenitor or osteoblast phenotype cells (OOP-1 cells) are negative for osteocalcin (OCN). It has been known in the art that OCN becomes expressed preferentially in mature osteoblasts. Hence, the absence of OCN expression signifies the less mature character of these cells.

In a further aspect, the invention provides osteoprogenitor, osteoblast or osteoblast phenotype cells (herein, "OOP-2 cells") characterised in that they co-express, i.e., are positive for, (1) at least one osteoblast marker chosen from alkaline phosphatase (ALP), more specifically ALP of the bone-liver-kidney type, procollagen type 1 amino-terminal propeptide (P1NP) and bone sialoprotein (BSP) with (2) the hematopoietic/endothelial progenitor marker CD34. Under (1): in a preferred embodiment, the said OOP-2 cells may express at least ALP; in further preferred embodiments, the said OOP-2 cells may express at least two markers chosen from ALP, P1NP and BSP, e.g., at least ALP and P1NP, at least ALP and BSP or at least P1NP and BSP; in a yet further preferred embodiment, the said OOP-2 cells may express at least all three of ALP, BSP and P1NP.

To the inventors' knowledge, osteoprogenitor or osteoblast phenotype cells expressing CD34 have never before been described, and the absence of CD34 is typically considered one of the features of bone marrow mesenchymal stem cells. Accordingly, the concomitant presence of at least one of ALP, P1NP or BSP with CD34 marks the osteoprogenitor or osteoblast phenotype cells of the invention (OOP-2 cells) as a new, previously undisclosed cell type. Moreover, this new cell type displays at least some of advantageous properties such as high proliferation rate, high mineralization rate and substantially absent propensity towards chondrocytic and adipocytic differentiation, which are particularly useful, e.g., in bone therapeutic context.

In a preferred embodiment, the said osteoprogenitor or osteoblast phenotype cells (OOP-2 cells) are negative for osteocalcin (OCN). It has been known in the art that OCN becomes expressed preferentially in mature osteoblasts. Hence, the absence of OCN expression signifies the less mature character of these cells.

The inventors also contemplate overlaps between the above described osteoprogenitor or osteoblast cell types of the invention. For example, in some embodiments, the OOP-1 cells may further co-express CD34. In other embodiments, the OOP-2 cells may further express at least one, e.g., one or both, of CD63 and CD166.

As mentioned, the invention also encompasses cell populations comprising the above osteoprogenitor or osteoblast phenotype cells of the invention, e.g., comprising the OOP-1 and/or OOP-2 cell types discussed above. An exemplary cell population may comprise at least 10%, preferably at least 30%, more preferably at least 50%, e.g., at least 60%, yet more preferably at least 70%, e.g., at least 80%, and even more preferably at least 90%, e.g., at least 95% of the OOP-1 and/or OOP-2 cell types. In preferred embodiments, the cell population may comprise less than 50%, preferably less than 40%, even more preferably less than 30%, yet more preferably less than 20% and still more preferably less than 10%, e.g., less than 7%, less than 5% or less than 2% of cell types other than the above OOP-1 and/or OOP-2 cell types.

In a preferred embodiment, the said cell population may also comprise endothelial cells or progenitors thereof. Preferably, such endothelial cells or progenitors may express at least one, e.g., at least two, or at least all three, of von Willebrand factor (vWF) VEGF and CD133. In a further embodiment, the said endothelial cells can also co-express CD34.

Advantageously, the inventors have realised that the presence of such endothelial cells or progenitors thereof in a cell population alongside osteoprogenitors or osteoblast phenotype cells of the invention may improve the engraftment of the said osteogenic lineage cells in patients, presumably, but without limitation, by instigating the formation of vessels supporting and oxygenating the implanted cells and tissues and/or by releasing growth factors, such as, e.g., VEGF.

In related aspects, the invention provides pharmaceutical formulations comprising the above defined cells and cell populations, and therapeutic uses thereof.

These and other features of the invention are further explained here below and in the appended claims, as well as illustrated by non-limiting examples.

DETAILED DESCRIPTION OF THE INVENTION

Figure 1:
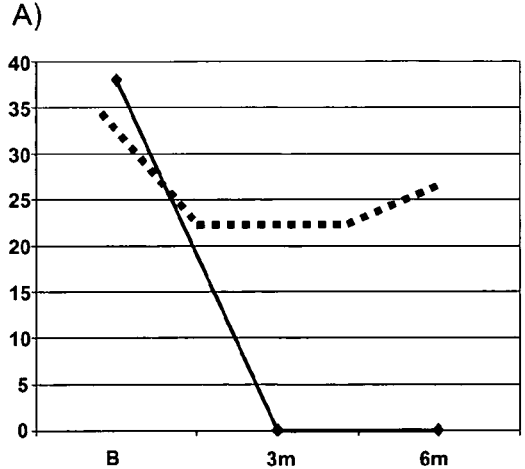
FIG. 1 shows results of injection of a cell population prepared according to the present invention in a patient with osteonecrosis of the femoral head (solid line with diamonds). A: VAS score; B: WOMAC score. "B"-baseline, "3 m"-3 months, "6 m"-6 months, dashed line-historical controls (control biopsy).
Figure 1:
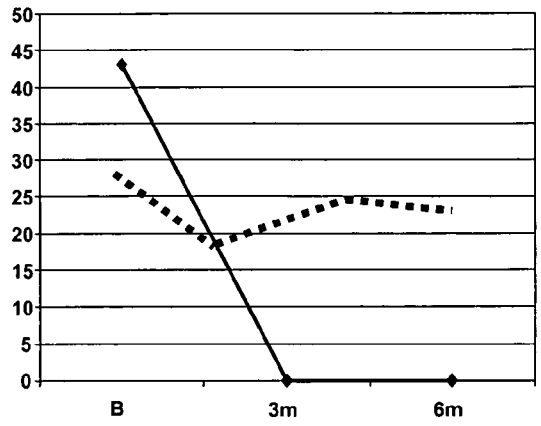

As used herein, the singular forms "a", "an", and "the" include both singular and plural referents unless the context clearly dictates otherwise. By way of example, "a cell" refers to one or more than one cell.

The terms "comprising", "comprises" and "comprised of" as used herein are synonymous with "including", "includes"

or "containing", "contains", and are inclusive or open-ended and do not exclude additional, non-recited members, elements or method steps.

The recitation of numerical ranges by endpoints includes all numbers and fractions subsumed within that range, as well as the recited endpoints.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

All documents cited in the present specification are hereby incorporated by reference in their entirety. In particular, the teachings of all documents herein specifically referred to are incorporated by reference.

Unless otherwise defined, all terms used in disclosing the invention, including technical and scientific terms, have the meaning as commonly understood by one of ordinary skill in the art to which this invention belongs.

1. Methods of Invention

As detailed in the Summary section, in an aspect, the invention relates to a method for obtaining osteoprogenitors, osteoblasts or osteoblast phenotype cells, as well as for obtaining cell populations comprising osteoprogenitors, osteoblasts or osteoblast phenotype cells, from human bone marrow stem cells in vitro or ex vivo, comprising contacting the bone marrow stem cells with human plasma or serum and a growth factor or a biologically active variant or derivative thereof.

Bone marrow is the soft tissue occupying medullar cavities of long bones, some haversian canals, and spaces between trabeculae of cancellous or spongy bone. Two types of bone marrow are conventionally distinguished: red, which is found in all bones in early life and in restricted locations in adulthood (e.g., in the spongy bone) and is primarily concerned with the production of blood cells (haematopoiesis); and yellow, which comprises primarily fat cells and connective tissue.

As a whole, bone marrow is a complex tissue comprised of hematopoietic stem cells, red and white blood cells and their precursors, mesenchymal stem cells (MSC), stromal cells and their precursors, and a group of cells including fibroblasts, reticulocytes, adipocytes, and cells which form a connective tissue network called "stroma".

Bone marrow cells contribute to many diverse tissues after systemic transplantation in both mice and humans. This capacity may reflect the activities of multiple stem cells present in bone marrow, such as, e.g., haematopoietic stem cells, mesenchymal stem cells and/or marrow multipotent stem cell. For example, Krause et al. (Cell 105: 369-377, 2001) showed that a single bone marrow derived stem cell can generate cells of both the haematopoietic and non-haematopoietic lineages. This is confirmed by Dominici et al. (PNAS 101 (32): 11761-6, 2004) who showed that hematopoietic cells and osteoblasts can be derived from a common marrow progenitor after bone marrow transplantation. In another example, U.S. Pat. No. 5,486,359 discloses the isolation from bone marrow of mesenchymal stem cells, capable of generating cells of mesenchymal lineages, e.g., of bone, cartilage, muscle, tendon, connective tissue, fat or marrow stroma. Further, Horwitz et al. (Nat Med 5(3): 309-13, 1999) showed that allogeneic bone marrow transplantation is effective in children with severe osteogenesis imperfecta. In that study, functional marrow-derived mesenchymal cells engrafted and contributed to the formation of new dense bone. As shown by Horwitz et al. (PNAS 99(13): 8932-7, 2002), the percentage of grafted osteoblasts was not significantly improved after the transplantation of only mesenchymal stem cells (plastic-adherent bone marrow cells), leading to the conclusion that bone marrow cells other than those in the adherent population, where mesenchymal stem cells are thought to reside, can be potent transplantable progenitors of osteoblasts. In view of the above, bone marrow may contain several types of stem cells with the potential to generate cells of the osteocytic (bone) lineage.

The term "bone marrow stem cell" or "BMSC" as used herein thus refers to any adult stem cell present in bone marrow, and particularly present in or (partly) isolated from a sample of bone marrow. A sample of bone marrow (BMSC) may be obtained, e.g., from iliac crest, femora, tibiae, spine, rib or other medullar spaces of a subject. The term BMSC also encompasses the progeny of BMSC, e.g., progeny obtained by in vitro or ex vivo propagation of BMSC obtained from a sample of a subject.

The term "stem cell" as used herein denotes any cell that, if exposed to appropriate conditions, is capable of giving rise to at least one, and preferably two or more different cell types. Such a stem cell may be capable of extensive, or perhaps indefinite, proliferation in vivo and, under specific conditions, also in vitro, wherein the progeny of such a stem cell may retain the phenotypic features and the proliferative capacity of the mother cell, or else may, if exposed to appropriate conditions, give rise to more specialized, i.e. more differentiated, cell(s). A stem cell is said to "give rise" to another, more differentiated, cell when, for example, the stem cell differentiates to become the other cell without previously undergoing cell division, or if the other cell is produced after one or more rounds of cell division and/or differentiation of the stem cell.

The term "adult stem cell" as used herein refers to a stem cell present in or obtained from an organism at the foetal stage or after birth.

Preferable bone marrow stem cells according to the invention have the potential of generating cells of at least the osteogenic (bone) lineage, such as, e.g., osteogenic cells and/or osteoprogenitors and/or pre-osteoblasts and/or osteoblasts and/or osteocytes, etc.

Preferably, at least some bone marrow stem cells according to the invention may also have the potential to generate further cells comprised in the cell populations resulting from the methods of the invention, such as, e.g., cells of endothelial lineage, for example endothelial progenitor cells and/or endothelial cells.

An exemplary, but non-limiting, type of BMSC having the potential of generating cells of at least the osteogenic lineage are mesenchymal stem cells. The term "mesenchymal stem cell" or "MSC" (also known as "marrow stromal cells") as used herein refers to an adult, mesoderm-derived stem cell that is capable of generating cells of mesenchymal lineages, typically of two or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. MSC may be isolated from, e.g., bone marrow, blood, umbilical cord, placenta, foetal yolk sac, skin (dermis), specifically foetal and adolescent skin, periosteum and adipose tissue. Human MSC, their isolation, in vitro expansion, and differentiation, have been described in, e.g., U.S. Pat. Nos. 5,486,359; 5,811,094; 5,736,396; 5,837,539; or 5,827,740. Any MSC described in the art and isolated by any method described in the art may be suitable in the present invention, provided such MSC are capable of generating cells of at least the osteocytic (bone) lineage, such as, e.g., osteogenic cells and/or osteoprogenitors and/or pre-osteoblasts and/or osteoblasts and/or osteocytes, etc.

Potentially, but without limitation, at least some MSC might also be able to generate further cells comprised in the cell populations resulting from the methods of the invention, such as, e.g., cells of endothelial lineage, for example endothelial progenitor cells and/or endothelial cells.

The term MSC also encompasses the progeny of MSC, e.g., progeny obtained by in vitro or ex vivo propagation of MSC obtained from a biological sample of an animal or human subject.

As shown in the examples, the present method of entails selecting those BMSC cells which, upon contacting with human plasma or serum and a growth factor or a biologically active variant or derivative thereof, adhere to a substrate surface, e.g., the surface of the culture vessel. It is known in the art that MSC can be isolated from bone marrow (or other sources) by selecting those (mononuclear) cells which can adhere to a substrate surface, e.g., plastic surface (indeed, MSC are sometimes referred to as plastic-adherent cells or colony forming unit fibroblasts). Therefore, without being limited to any hypothesis, the present inventors speculate that in the present method, MSC may at least partly contribute to obtaining of osteoblasts or osteoblast phenotype cells from BMSC.

Therefore, in an aspect, the present invention also contemplates a method for obtaining osteoblasts or osteoblast phenotype cells from human mesenchymal stem cells in vitro or ex vivo, comprising contacting the MSC with human plasma or serum and a growth factor.

MSC may be comprised in a biological sample, e.g., in a sample comprising BMSC, or may be at least partly isolated therefrom as known in the art. Moreover, MSC may be at least partly isolated from bone marrow or from sources comprising MSC other than bone marrow, e.g., blood, umbilical cord, placenta, foetal yolk sac, skin (dermis), specifically foetal and adolescent skin, periosteum and adipose tissue.

In a preferred embodiment, BMSC or MSC present in or at least partly isolated from the biological sample may be contacted with human plasma or serum and a growth factor or a biologically active variant or derivative thereof, without prior propagation in conditions which allow for cell growth and doubling of BMSC or MSC without differentiation.

It is further known that preparations of MSC from bone marrow comprise a subpopulation of cells which are small, proliferate rapidly, undergo cyclical renewal when re-plated at low density and are precursors of more mature MSC in the same culture. This subpopulation of cells is termed "rapidly self-renewing cells" and may have at least two components identified as RS-1 and RS-2 (Colter et al. PNAS 97(7): 3213-8, 2000; incorporated by reference herein). Therefore, without being limited to any hypothesis, the present inventors speculate that in the present method, RS cells as described by Colter et al. 2000 may at least in part contribute to obtaining of osteoprogenitors, osteoblasts or osteoblast phenotype cells from BMSC, possibly leading through an intermediate of more mature MSC. Potentially, but without limitation, the inventors speculate that RS cells might also be able to generate further cells comprised in the cell populations resulting from the methods of the invention, such as, e.g., cells of endothelial lineage, for example endothelial progenitor cells and/or endothelial cells.

Accordingly, in an embodiment, the present invention also contemplates a method for obtaining osteoprogenitors, osteoblasts or osteoblast phenotype cells, or for obtaining cell populations comprising such, from human rapidly self-renewing cells (RS) in vitro or ex vivo, comprising contacting the RS with human plasma or serum and a growth factor.

It is further known that bone marrow contains a precursor cell population termed "side population" (SP). These cells are identified as $CD34^{low/neg}$ hematopoietic precursors, but have remarkable plasticity in terms of regenerating hematopoietic as well as non-hematopoietic tissue (Goodell et al. 1997. Nat Med 3(12):1337-45; incorporated by reference herein). Therefore, without being limited to any hypothesis, the present inventors speculate that in the present method, SP cells as described by Goodell et al. 1997 may at least in part contribute to obtaining of osteoprogenitors, osteoblasts or osteoblast phenotype cells from BMSC, possibly leading through an intermediate of more mature MSC. Potentially, but without limitation, the inventors speculate that SP cells might also be able to generate further cells comprised in the cell populations resulting from the methods of the invention, such as, e.g., cells of endothelial lineage, for example endothelial progenitor cells and/or endothelial cells.

Accordingly, in an embodiment, the present invention also contemplates a method for obtaining osteoprogenitors, osteoblasts or osteoblast phenotype cells, or for obtaining cell populations comprising such, from human side population cells (SP) in vitro or ex vivo, comprising contacting the SP with human plasma or serum and a growth factor.

It is further known that bone marrow comprises a population of osteogenic precursor cells which are initially identified by their low density (e.g., upon density gradient centrifugation), non-adherent nature and low-level of expression of osteogenic markers (Long et al. 1995. J Clin Invest. 1995 February; 95(2):881-7; U.S. Pat. No. 5,972,703; incorporated by reference herein). However, as such cells are induced to differentiate towards osteoblasts, they also become adherent to substrate surface. Therefore, without being limited to any hypothesis, the present inventors speculate that in the present method, osteogenic precursors as described by Long et al. 1995 may at least in part contribute to obtaining of osteoprogenitors, osteoblasts or osteoblast phenotype cells from BMSC.

Accordingly, in an embodiment, the present invention also contemplates a method for obtaining osteoprogenitors, osteoblasts or osteoblast phenotype cells, or for obtaining a cell population comprising such, from human osteogenic precursors (OP) in vitro or ex vivo, comprising contacting the OP with human plasma or serum and a growth factor.

It is further known that bone marrow comprises a population of primitive precursor cells which can generate cells of both the haematopoietic and non-haematopoietic lineages (Krause et al. 2001. Cell 105:369-377; Dominici et al. 2004. PNAS 101(32): 11761-6). Therefore, without being limited to any hypothesis, the present inventors speculate that in the present method, such primitive precursors may at least in part contribute to obtaining of osteoprogenitors, osteoblasts or osteoblast phenotype cells from BMSC, possibly leading through an intermediate of more mature MSC. Potentially, but without limitation, the inventors speculate that such primitive precursors might also be able to generate further cells comprised in the cell populations resulting from the methods of the invention, such as, e.g., cells of endothelial lineage, for example endothelial progenitor cells and/or endothelial cells.

It is to be understood that, given the complexity of bone marrow stem cell populations, the present invention should not be seen as limited to one or more particular BMSC types. Rather, in the present method, one or more BMSC cell types, e.g., as described above, may contribute, perhaps to different extent, to obtaining osteoprogenitors, osteoblasts or osteoblast phenotype cells, or to obtaining cell populations comprising such. On the other hand, it is to be understood that the present method may also employ a particular BMSC population, e.g., MSC, at least partly isolated from other BMSC populations.

According to the present aspect, the obtaining of osteoprogenitors, osteoblasts or osteoblast phenotype cells from human bone marrow stem cells is in vitro or ex vivo. The term "in vitro" as used herein is to denote outside, or external to, animal or human body. The term "in vitro" as used herein should be understood to include "ex vivo". The term "ex vivo" typically refers to tissues or cells removed from an animal or human body and maintained or propagated outside the body, e.g., in a culture vessel.

In an embodiment, BMSC are obtained from a biological sample of a human subject.

The term "biological sample" or "sample" as used herein refers to a sample obtained from a biological source, e.g., from an organism, such as an animal or human subject, cell culture, tissue sample, etc. A biological sample of an animal or human subject refers to a sample removed from an animal or human subject and comprising cells thereof. The biological sample of an animal or human subject may comprise one or more tissue types and may comprise cells of one or more tissue types. Methods of obtaining biological samples of an animal or human subject are well known in the art, e.g., tissue biopsy or drawing blood.

A useful biological sample of a human subject comprises bone marrow stem cells thereof. Such sample may be typically obtained from bone marrow, e.g., from iliac crest, femora, tibiae, spine, rib or other medullar spaces of a subject. Another useful biological sample comprises mesenchymal stem cells, and may be derived, e.g., from blood, umbilical cord, placenta, foetal yolk sac, skin (dermis), specifically foetal and adolescent skin, periosteum, or adipose tissue of a subject.

The term "subject" as used herein refers to a eukaryotic organism, in particular an animal or human organism. Animal subjects include prenatal forms of animals, such as, e.g., foetuses. Human subjects may include foetuses, and not embryos.

In another embodiment, BMSC are obtained from a human subject who is at risk for or has a bone-related disorder. The present inventors have realised that administering osteoblasts or osteoblast phenotype cells obtained from the BMSC of such subject according to the methods of the invention can be useful for treating the bone-related disorder in the said subject, e.g., by de novo bone formation or increasing bone density.

Accordingly, the term "bone-related disorder" as used herein refers to any type of bone disease, the treatment of which may benefit from the administration of osteogenic lineage cells, e.g., osteoprogenitors, osteoblasts or osteoblast phenotype cells to a subject having the disorder. In particular, such disorders may be characterised, e.g., by decreased bone formation or excessive bone resorption, by decreased number, viability or function of osteoblasts or osteocytes present in the bone, decreased bone mass in a subject, thinning of bone, compromised bone strength or elasticity, etc.

By way of example, but not limitation, bone-related disorders which can benefit from administration of osteoblasts or osteoblast phenotype cells of the present invention may include local or systemic disorders, such as, any type of osteoporosis or osteopenia, e.g., primary, postmenopausal, senile, corticoid-induced, any secondary, mono- or multisite osteonecrosis, any type of fracture, e.g., non-union, malunion, delayed union fractures or compression, conditions requiring bone fusion (e.g., spinal fusions and rebuilding), maxillo-facial fractures, bone reconstruction, e.g., after traumatic injury or cancer surgery, cranio-facial bone reconstruction, osteogenesis imperfecta, osteolytic bone cancer, Paget's Disease, endocrinological disorders, hypophsophatemia, hypocalcemia, renal osteodystrophy, osteomalacia, adynamic bone disease, rheumatoid arthritis, hyperparathyroidism, primary hyperparathyroidism, secondary hyperparathyroidism, periodontal disease, Gorham-Stout disease and McCune-Albright syndrome.

As recited above, the method of the present invention is for obtaining osteoprogenitors, osteoblasts or osteoblast phenotype cells, or cell populations comprising such, from BMSC.

As used herein in the context of the methods of the invention, the recitation osteoprogenitors, osteoblasts or osteoblast phenotype cells generally encompass cells which can contribute to, or are capable of developing to cells which can contribute to, the formation of bone material or bone matrix. It is to be understood that this aspect of the invention provides methods resulting in cells and cell populations which, as experimentally substantiated by the inventors, are useful for restoring bone formation in therapeutic settings. Consequently, the recitation osteoprogenitors, osteoblasts or osteoblast phenotype cells should be construed as wishing to encompass any such useful cells of the osteogenic lineage resulting from the methods of the invention.

The present disclosure provides sufficient guidance to perform the method of the invention, such as to arrive at cells and cell populations contemplated herein and generally referred to by the above recitation. By means of verification whether desired cells or cell populations have been obtained, a skilled person can apply, e.g., the phenotypical assessment methods disclosed in the examples or further tests in the art. Nevertheless, by further guidance and not limitation, an osteoprogenitor, osteoblast or osteoblast phenotype cell may encompass any cell of the osteogenic cell lineage which will have at least one characteristic, and may display at least two, at least three, at least four or at least five characteristics, from the following list: (a) positive for CD90, CD73 and CD105 (b) positive for alkaline phosphatase (ALP) (more specifically, ALP of the bone-liver-kidney type); (c) positive for osteocalcin (specific for mature osteoblasts); (d) density between 1.050 and 1.090 g/cm$^3$; (e) positive for osteonectin (positive in osteoblasts and precursors); (f) a cell diameter between 6 to 70 µm and substantially cuboidal shape; (g) positive for type I collagen (procollagen) and/or for vimentin and/or bone sialoprotein; (h) positive for other osteoblast-specific markers, such as BMP receptors, PTH receptors; (i) evidence of ability to mineralize the external surroundings, or synthesize calcium-containing extracellular matrix, when exposed to osteogenic medium (Jaiswal et al. 1997. J Cell Biochem 64: 295-312).

The expression of the above cell-specific markers can be detected using any suitable immunological technique known in the art, such as immuno-cytochemistry or affinity adsorption, Western blot analysis, FACS, ELISA, etc., or by any suitable biochemical assay of enzyme activity (e.g., for ALP), or by any suitable technique of measuring the quantity of the marker mRNA, e.g., Northern blot, semi-quantitative or quantitative RT-PCR, etc. Sequence data for markers listed in this disclosure are known and can be obtained from public databases such as GenBank. Calcium accumulation inside cells and deposition into matrix proteins can be measured by culturing in $^{45}Ca^{2+}$, washing and re-culturing, and then determining any radioactivity present inside the cell or deposited into the extracellular matrix (U.S. Pat. No. 5,972,703), or by assaying culture substrate for mineralization using a $Ca^{2+}$ assay kit (Sigma Kit #587), or as described in the examples.

Wherein a cell is said to be positive for a particular marker, this means that a skilled person will conclude the presence of a distinct signal for that marker when carrying out the appropriate measurement. Where the method allows for quantitative assessment of the marker, positive cells may generate a signal that is at least 2-fold higher than such signal generated by control cells (e.g., by BMSC cells before applying the method of the present invention, or by any other non-osteogenic cells), e.g., at least 4-fold, at least 10-fold, at least 20-fold, at least 30-fold, at least 40-fold or at least 50-fold higher.

As explained, BMSC present in or at least partly isolated from the biological sample are contacted with human plasma or serum and a growth factor or a biologically active variant or derivative thereof, in order to obtain osteoprogenitors, osteoblasts or osteoblast phenotype cells.

A skilled person appreciates that human plasma and serum are complex biological compositions, which may comprise one or more growth factors, cytokines or hormones. Therefore, the term "contacted with human plasma or serum and a growth factor or a biologically active variant or derivative thereof" denotes that the said growth factor or a biologically active variant or derivative thereof is provided in addition to, i.e., exogenously to or in supplement to, the plasma or serum. Hence, BMSC are contacted, besides the growth factors that may be comprised in the plasma or serum, with a growth factor or a biologically active variant or derivative thereof provided in addition to, i.e., exogenously to or in supplement to, the plasma or serum.

The said growth factor or a biologically active variant or derivative thereof may be one that is not present in the plasma or serum. In such case, BMSC are contacted with a (i.e., the said) growth factor or a biologically active variant or derivative thereof with which they would not be contacted if they were contacted with the plasma or serum alone. The said growth factor or a biologically active variant or derivative thereof may also be one that is present in the plasma or serum. In such case, BMSC are contacted with a greater amount or concentration of a (i.e., the said) growth factor or a biologically active variant or derivative thereof than if they were contacted with the plasma or serum alone.

The term "growth factor" as used herein refers to a biologically active substance which influences proliferation, growth, differentiation, survival and/or migration of various cell types, and may effect developmental, morphological and functional changes in an organism, either alone or when modulated by other substances. A growth factor may typically act by binding, as a ligand, to a receptor (e.g., surface or intracellular receptor) present in cells responsive to the growth factor. A growth factor herein may be particularly a proteinaceous entity comprising one or more polypeptide chains.

By means of example and not limitation, the term "growth factor" encompasses the members of the fibroblast growth factor (FGF) family, bone morphogenic protein (BMP) family, platelet derived growth factor (PDGF) family, transforming growth factor beta (TGFbeta) family, nerve growth factor (NGF) family, the epidermal growth factor (EGF) family, the insulin related growth factor (IGF) family, the hepatocyte growth factor (HGF) family, hematopoietic growth factors (HeGFs), the platelet-derived endothelial cell growth factor (PD-ECGF), angiopoietin, vascular endothelial growth factor (VEGF) family, glucocorticoids, and the like.

In a preferred embodiment, the growth factor is a member of the fibroblast growth factor (FGF) family. In a further embodiment, the said member of the FGF family is chosen from the group consisting of acidic and basic FGF, FGF-1 and FGF-2, respectively, int2 (FGF-3), hst (FGF-4), FGF-5, hst2 (FGF-6), keratinocyte growth factor (FGF-7), androgen-induced growth factor (FGF-8); glia-activating factor (FGF-9) and any of FGF-10 to 23.

In a preferred embodiment, the fibroblast growth factor is basic FGF, also denoted FGF-b, FGF-2, BFGF, HBGH-2, prostatropin, or heparin-binding growth factor 2 precursor (HBGF-2). The inventors have realised that FGF-b is particularly effective in the method of the present invention.

In an embodiment, FGF-2 or a biologically active variant or derivative thereof is the only growth factor, provided exogenously to those potentially present in human serum or plasma, with which BMSC are contacted in the method of the invention.

In a further embodiment, BMSC are contacted with FGF-2 or a biologically active variant or derivative thereof and one or more additional growth factors other than FGF-2. Preferably, the said one or more additional growth factors do not include EGF.

In another embodiment, the growth factor is a member of the bone morphogenic protein (BMP) family. In a further embodiment, the said member of the BMP family is any chosen from the group consisting of BMP-2, BMP-3, BMP-4, BMP-5, BMP-3b/GDF-10, BMP-6, BMP-7, BMP-8 and BMP-15.

In an embodiment, the growth factor is a member of the platelet derived growth factor (PDGF) family. In a further embodiment, the said member of the PDGF family is any chosen from the group consisting of neuropilin-2, PDGF, PDGF-A, PDGF-B, PDGF-C, PDGF-D, PDGF-AB and PIGF.

In an embodiment, the growth factor is a member of the transforming growth factor beta (TGFbeta) family. In a further embodiment, the said member of the TGFbeta family is any chosen from the group consisting of TGF-beta-1, TGF-beta-2, TGF-beta-3, TGF-beta-4, GDF1 (Growth/differentiation factor 1), GDF-2, GDF-3, GDF-5, GDF-6, GDF-7, GDF-8, GDF-9, GDF-11, GDF-15, INHA (inhibin alpha chain), INHBA (inhibin beta A chain), INHBB (inhibin beta B chain), INHBC (inhibin beta C chain), INHBE (inhibin beta E chain), MIS (Muellerian-inhibiting factor), and further of members of GDNF subfamily, including GDNF (glial cell line-derived neurotrophic factor), NRTN (neurturin), PSPN (persephin).

In an embodiment, the growth factor is a member of the nerve growth factor (NGF) family. In a further embodiment, the said member of the NGF family is any chosen from the group consisting of BDNF (brain-derived neurotrophic factor), NGF (beta-nerve growth factor), NT3 (neurotrophin-3) and NT5.

In an embodiment, the growth factor is a member of the epidermal growth factor (EGF) family. In a further embodiment, the said member of the EGF family is any chosen from the group consisting of amphiregulin, betacellulin, EGF, epiregulin, HB-EGF (heparin-binding EGF-like growth factor), NRG1 (neuregulin-1) isoform GGF2, NRG1 isoform SMDF, NRG1-alpha, NRG1-beta, TGFalpha, Tomoregulin-1 and TMEFF2.

In an embodiment, the growth factor is a member of the insulin related growth factor (IGF) family. In a further embodiment, the said member of the IGF family is any chosen from the group consisting of insulin, IGF1A (insulin-like growth factor 1A), IGF1B, IGF2, INSL3 (insulin-like 3), INSL5, INSL6 and relaxin.

In an embodiment, the growth factor is a member of the vascular endothelial growth factor (VEGF) family. In a further embodiment, the said member of the VEGF family is any chosen from the group consisting of VEGF, VEGF-B, VEGF-C and VEGF-D.

In an embodiment, the growth factor is a glucocorticoid. In a further embodiment, the said glucocorticoid is any chosen from the group consisting of dexamethasone, hydrocortisone, prednisolone, methylprednisolone, prednisone, triamcinolone, corticosterone, fluocinolone, cortisone, betamethasone.

In a preferred embodiment, the growth factor used in the present method is a human growth factor. As used herein, the term "human growth factor" refers to a growth factor substantially the same as a naturally occurring human growth factor. For example, where the growth factor is a proteinaceous entity, the constituent peptide(s) or polypeptide(s) thereof may have primary amino acid sequence identical to a naturally occurring human growth factor. The use of human growth factors in the present method is preferred, as such growth factors are expected to elicit a desirable effect on cellular function.

The term "naturally occurring" is used to describe an object or entity that can be found in nature as distinct from being artificially produced by man. For example, a polypeptide sequence present in an organism, which can be isolated from a source in nature and which has not been intentionally modified by man in the laboratory, is naturally occurring. When referring to a particular entity, e.g., to a polypeptide or protein, the term encompasses all forms and variants thereof which occur in nature, e.g., due to a normal variation between individuals. For example, when referring to a proteinaceous growth factor, the term "naturally occurring" encompasses growth factors having differences in the primary sequence of their constituent peptide(s) or polypeptide(s) due to normal allelic variation between individuals.

The present method may employ a biologically active variant or derivative of a growth factor. In the method of the invention, "biologically active" variants or derivatives of a growth factor achieve at least about the same degree of obtaining osteoblasts or osteoblast phenotype cells from BMSC as the respective growth factor, when other conditions are substantially the same.

Where a growth factor exerts its effects by binding to its cognate receptor, biologically active variants or derivatives of the said growth factor may display affinity and/or specificity for binding to that cognate receptor, which is at least about as high as the affinity and/or specificity of the growth factor for binding thereto. For example, the said biologically active variants or derivatives may have affinity and/or specificity for binding to the cognate receptor which is at least 80%, e.g., at least 85%, preferably at least 90%, e.g., at least 90%, or even 100% or more of the affinity and/or specificity of the respective growth factor for binding to that receptor. The above parameters of the binding may be readily determined by a skilled person using in vitro or cellular assays which are known per se.

Where the activity of a given growth factor can be readily measured in an established assay, e.g., an in vitro or cellular assay (such as, for example, measurement of mitogenic activity in cell culture), biologically active variants or derivatives of the said growth factor may display activity in such assays, which is at least about as high as the activity of the growth factor. For example, the said biologically active variants or derivatives may show activity which is at least 80%, e.g., at least 85%, preferably at least 90%, e.g., at least 90%, or even 100% or more of the activity of the respective growth factor.

A "variant" of a polypeptide has an amino acid sequence which is substantially identical (i.e., largely but not wholly identical) to the amino acid sequence of the polypeptide. Herein, "substantially identical" refers to at least 85% identical, e.g., at least 90% identical, preferably at least 95% identical, e.g., least 99% identical. Sequence differences may result from insertion (addition), deletion and/or substitution of one of more amino acids.

Sequence identity between two polypeptides can be determined by aligning the amino acid sequences of the polypeptides and scoring, on one hand, the number of positions in the alignment at which the polypeptides contain the same amino acid residue and, on the other hand, the number of positions in the alignment at which the two polypeptides differ in their sequence. The two polypeptides differ in their sequence at a given position in the alignment when the polypeptides contain different amino acid residues at that position (amino acid substitution), or when one of the polypeptides contains an amino acid residue at that position while the other one does not or vice versa (amino acid insertion/addition or deletion).

Sequence identity is calculated as the proportion (percentage) of positions in the alignment at which the polypeptides contain the same amino acid residue versus the total number of positions in the alignment.

At least some of the differences between the amino acid sequences of a variant and of the respective polypeptide with which the variant is substantially identical, can involve amino acid substitutions. Preferably, at least 85%, e.g., at least 90%, more preferably at least 95%, e.g., 100% of the said differences can be amino acid substitutions. Preferably, the said amino acid substitutions may be conservative. The term "conservative substitution" as used herein denotes that one amino acid residue has been replaced by another, biologically similar amino acid residue. Non-limiting examples of conservative substitutions include the substitution of one hydrophobic amino acid residue, such as isoleucine, valine, leucine or methionine for another, or the substitution of one polar residue for another, such as between arginine and lysine, between glutamic and aspartic acids or between glutamine and asparagine, and the like.

A variant growth factor may be comprised of one or more peptide(s) or polypeptide(s), at least one of which is a variant as defined above of the respective constituent peptide or polypeptide of the growth factor.

A "derivative" of a polypeptide may be derivatised by chemical alteration of one or mode amino acid residues and/or addition of one or more moieties at one or more amino acid residues, e.g., by glycosylation, phosphorylation, acylation, acetylation, sulphation, lipidation, alkylation, etc. Typically, less than 50%, e.g., less than 40%, preferably less than 30%, e.g., less than 20%, more preferably less than 15%, e.g., less than 10% or less than 5%, e.g., less than 4%, 3%, 2% or 1% of amino acids in a derivative polypeptide may be so derivatised. A derivative proteinaceous growth factor may be comprised of one or more peptide(s) or polypeptide(s), at least one of which may be derivatised on at least one amino acid residue.

In another embodiment, the growth factor used in the present method may be a non-human animal growth factor, and particularly a non-human mammal growth factor, or a biologically active variant or derivative thereof. As used herein, the terms "non-human animal growth factor" and "non-human mammal growth factor" refer to a growth factor substantially the same as, respectively, a naturally occurring non-human animal or non-human mammal growth factor. For example, where the growth factor is a proteinaceous entity, the constituent peptide(s) or polypeptide(s) thereof may have primary amino acid sequence identical to a naturally occurring non-human animal or non-human mammal growth factor. A skilled person will understand that non-human animal or non-human mammal growth factors may be applicable in the present method, albeit to a lesser extent than human animal growth factors, since the latter are of the same origin as the BMSC cells. In particular, non-human animal or non-human mammal growth factors may be used if they elicit the desired effect, e.g., an effect similar to an (analogous) human growth factor.

In a preferred embodiment, the growth factor or a biologically active variant or derivative thereof is recombinant, i.e., produced by a host organism through the expression of a recombinant nucleic acid molecule, which has been introduced into the host organism or an ancestor thereof, and which comprises a sequence encoding the said polypeptide. The term "recombinant nucleic acid molecule" as used herein refers to a nucleic acid molecule (e.g., a DNA or cDNA molecule) which is comprised of segments joined together using recombinant DNA technology.

The use of recombinantly expressed growth factors or biologically active variants or derivatives thereof may be particularly advantageous. For example, if the growth factor is a human growth factor, it may be more readily prepared from a recombinant source than by isolation from human biological material. Moreover, isolation of growth factors form human or animal material may entail the risk of transmission of pathogenic agents. Such risk can be more effectively controlled or eliminated during recombinant expression, particularly if this employs cell expression systems that can be routinely inspected for the presence of pathogenic agents. Advantageously, such risk can be further diminished if the cell expression systems are distant from humans, e.g., bacteria cells, yeast cells, plant cells or insect cells, since pathogenic agents possibly present in such cultures would be less likely to harm human cells or humans.

Suitable expression systems, e.g., expression vectors, such as plasmid and viral vectors; host organisms, such as bacteria (e.g., *E. coli, S. tymphimurium, Serratia marcescens, Bacillus subtilis*), yeast (e.g., *S. cerevisiae* and *Pichia pastoris*), cultured plant cells (e.g., from *Arabidopsis thaliana* and *Nicotiana tobaccum*) and animal cells (e.g., mammalian cells and insect cells), and multi-cellular organisms, such as plants or animals; and procedures for isolation of the expressed recombinantly produced proteins, such as growth factors or biologically active variants or derivatives thereof, are known in the art. Reference is made to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in Molecular Biology and Short Protocols in Molecular Biology, 3rd Ed." (F. M. Ausubel et al., eds., 1987 & 1995); Recombinant DNA Methodology II (R. Wu ed., Academic Press 1995), incorporated by reference herein. Recombinant growth factors are also commonly commercially available (e.g., from Sigma, Biological Industries, R&D Systems, Peprotech, etc.).

The term "plasma" is as conventionally defined. Plasma is usually obtained from a sample of whole blood, which is provided or contacted with an anticoagulant, such as heparin, citrate (e.g., sodium citrate or acid citrate dextrose), oxalate or EDTA, upon or shortly after drawing the blood sample, to prevent clotting. Subsequently, cellular components of the blood sample are separated from the liquid component (plasma) by an appropriate technique, typically by centrifugation. The term "plasma" therefore refers to a composition which does not form part of a human or animal body.

The term "serum" is as conventionally defined. Serum can be usually obtained from a sample of whole blood by first allowing clotting to take place in the sample and subsequently separating the so formed clot and cellular components of the blood sample from the liquid component (serum) by an appropriate technique, typically by centrifugation. Clotting can be facilitated by an inert catalyst, e.g., glass beads or powder. Advantageously, serum can be prepared using serum-separating tubes (SST) known in the art, which contain the inert catalyst to facilitate clotting and further include a gel with density designed to become positioned between the liquid component and the clot and cellular components after centrifugation, thus simplifying separation. Alternatively, serum can be obtained from plasma by removing the anticoagulant and fibrin. The term "serum" hence refers to a composition which does not form part of a human or animal body.

The isolated plasma or serum can be used directly in the method of the present invention. They can also be appropriately stored for a later use in the method of the present invention. Typically, plasma or serum can be stored for shorter time periods, e.g., up to about 1-2 weeks, at a temperature above the respective freezing points of plasma or serum, but below ambient temperature. Usually, this temperature will be about 15° C. or less, preferably about 10° C. or less, more preferably about 5° C. or less, e.g., about 5° C., 4° C., 3° C., 2° C. or about 1° C., most preferably about 5° C. or about 4° C. Alternatively, plasma or serum can be stored at below their respective freezing points, i.e., by freeze storage. As usual in the art, advantageous temperatures for freeze storage of plasma or serum can be about −70° C. or less, e.g., about −75° C. less or about −80° C. or less. Such temperatures may advantageously prevent any thawing of the stored plasma or serum, thereby preserving the quality thereof. Freeze storage can be used irrespective of the time period for which the plasma or serum need to be stored, but may be particularly suitable if longer storage is required, e.g., for longer than a few days or for longer than 1-2 weeks.

Prior to storage or use, the isolated plasma or serum can be heat inactivated. Heat inactivation is used in the art mainly to remove the complement. Where the present method employs plasma or serum autologous to the cells cultured in the presence thereof, it may be unnecessary to heat inactivate the plasma or serum. Where the plasma or serum is at least partly allogeneic to the cultured cells, it may be advantageous to heat inactivate the plasma or serum. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure.

Optionally, the plasma or serum may also be sterilised prior to storage or use. Usual means of sterilisation may involve, e.g., filtration through one or more filters with pore size smaller than 1 µm, preferably smaller than 0.5 µm, e.g., smaller than 0.45 µm, 0.40 µm, 0.35 µm, 0.30 µm or 0.25 µm, more preferably 0.2 µm or smaller, e.g., 0.15 µm or smaller, 0.10 µm or smaller.

In an embodiment, the present method employs human plasma or serum which is autologous to human BMSC contacted therewith. The term "autologous" with reference to plasma or serum denotes that the plasma or serum is obtained from the same subject as are BMSC to be contacted with the said plasma or serum. The present inventors have realised that the use of autologous plasma or serum provides advantageous conditions for obtaining osteoblasts and osteoblast phenotype cells from BMSC. In addition, when the obtained osteoblasts or osteoblast phenotype cells are to be administered to the same human subject from which the BMSC were obtained, the use of autologous plasma or serum may ensure optimal acceptance of the cells by the subject and/or avoid accidental transmission of infectious agents from, e.g., other sera.

In another embodiment, the method may employ human plasma or serum which is "homologous" to human BMSC contacted therewith, i.e., obtained from one or more (pooled) human subjects other than the subject from which the BMSC are obtained.

In a further embodiment, the method may employ a mixture of autologous and homologous plasma or sera as defined above.

The term "contacting" as used herein means bringing together, either directly or indirectly, one or more molecules, components or materials with another, thereby facilitating interactions there between. Typically, a growth factor or a biologically active variant or derivative thereof, and human plasma or serum, may be contacted with BMSC by means of their inclusion in the media, in which the BMSC are cultured.

In embodiments, human plasma or serum may be included in the media at a proportion (volume of serum/volume of medium) between 0.5% and 30%, preferably between 1% and 20%, more preferably between 2% and 10%, such as between 5% and 10%, e.g., at about 5%, 6%, 7%, 8%, 9% or 10%. The inventors have surprisingly realised that human plasma or serum in a relatively low amount, e.g., at about 5 volume % or below, e.g. between 1% and 5%, between 2% and 5%, between 3% and 5% or between 4% and 5% may be sufficient for obtaining osteoprogenitors, osteoblasts or osteoblast phenotype cells from BMSC. This allows to advantageously decrease the volume of plasma or serum that needs to be obtained from a donor (e.g., from a patient in case of autologous plasma or serum) in order to culture the BMSC.

A growth factor or a biologically active variant or derivative thereof may be included in the media at a concentration sufficient, in combination with human plasma or serum included in the same media at one of the above indicated proportions, to induce differentiation of BMSC into osteoblasts or osteoblast phenotype cells, thereby obtaining the latter. Typically, the growth factor, e.g., FGF-2, or a biologically active variant or derivative thereof can be included in the media at a concentration of between 0.01 and 100 ng/ml, preferably between 0.1 and 50 ng/ml, e.g., between 0.5 and 30 ng/ml, more preferably between 1 and 20 ng/ml, such as between 1 and 10 ng/ml, e.g., preferably less than 5 ng/ml, e.g., 1, 2, 3, 4, or 5 ng/ml. Where a growth factor would be glucocorticoid, e.g., dexamethasone, such concentration may preferably be between $10^{-9}$ to $10^{-5}$ mMol. It will be understood that the above concentrations refer to that growth factor or a biologically active variant or derivative thereof, which is provided in addition to, i.e., exogenously to or in supplement to, the plasma or serum (see elsewhere in the specification).

In a preferred embodiment, FGF-2 or a biologically active variant or derivative thereof is included at a concentration lower than 20 ng/ml, preferably lower than 10 ng/ml, yet more preferably lower than 5 ng/ml, e.g., at 1, 2, 3, 4 or 5 ng/ml. The inventors hypothesize that such lower FGF-2 concentration may be particularly preferred for achieving differentiation.

In an embodiment, the above concentrations may refer to the total concentration of the said growth factor or a biologically active variant or derivative thereof in the medium, i.e., to the sum concentration of the growth factor or a biologically active variant or derivative thereof as contributed by the plasma or serum and as provided in addition thereto.

In another embodiment, the above concentrations may refer to the concentration of the said growth factor or a biologically active variant or derivative thereof as provided in addition to that already contributed by the plasma or serum. Understandably, if the growth factor to-be-added is normally not present (not detectable) in the plasma or serum, the total and added concentration of the growth factor will be (substantially) the same.

In an embodiment, BMSC may be continuously contacted with human plasma or serum and a growth factor or a biologically active variant or derivative thereof, for a time period sufficient to induce differentiation of BMSC into osteoprogenitors, osteoblasts or osteoblast phenotype cells, thereby obtaining the latter. The term "continuously contacted" may mean that the said components are included in all media, in which the BMSC, the progeny thereof and/or or cells derived therefrom, are cultured during the said time period. Typically, human plasma or serum and the growth factor or a biologically active variant or derivative thereof may be supplied at substantially identical respective concentrations in all (fresh) media used for culturing the BMSC during the said time period.

Hence, typically, t=0 days would correspond to the time point when isolated BMSC are first plated in the presence of a growth hormone and human serum or plasma (primary culture).

In embodiments, the above exposure time period may be at least 5 days, preferably at least 10 days, more preferably at least 15 days and even more preferably at least 18 days, e.g., at least 20 days. For example, the time period may be between 5 and 30 days, preferably between 10 and 30 days, more preferably between 15 and 25 days, and even more preferably about 20 days, e.g., 20, 21, 22 or so days. For example, in a preferred embodiment, the time period may be between 12 and 16 days, e.g., 12, 13, 14, 15 or 16 days, particularly preferably about 14 days. In another preferred embodiment, the time period may be between 18 and 24 days, e.g., 18, 19, 20, 21, 22, 23 or 24 days, particularly preferably about 21 days.

In further embodiments, the above time period may involve one or more passages of the cells, such as, 1, 2, 3, 4 or more passages, and preferably it would involve 1, 2 or 3 passages, even more preferably 1 or 2 passages, e.g., 1 passage. The passage number refers to the number of times that a cell population has been removed from a culture vessel and undergone a subculture, i.e., a passage. As will be understood by a skilled person, cells grown in culture are typically passaged when they have reached a given degree of confluence. For example, if cells are present as monolayers, they may be passaged when their confluence is 60% or more, e.g., 70% or more, 80% or more, or 90% or more, or even 100%. The cells may be typically passaged at a ratio between of ⅛ to ⅔, such as ¼ to ½. This ratio expresses the proportion of cells which are introduced into the same volume of medium after passaging. If cells are present in colonies, they may be passaged, e.g., after a given number of days in culture, e.g., at between 4 and 20 days, e.g., between 8 and 15 days, more preferably between 10 to 15 days, e.g., at 10, 11, 12, 13, or 14 days. For example, they may be passaged once the average number of cells per colony is 20 or more, or 50 or more, or 100 or more, 500 or more.

In a particular preferred embodiment, where the total time of contacting the cells with a growth factor, especially FGF-2, and human serum or plasma is, preferably, between 12 and 16 days, the primary plated BMSC need not be passaged, but may be directly collected. In another preferred embodiment, where the total time of contacting the BMSC with a growth factor, especially FGF-2, and human serum or plasma is, preferably, between about 18 and about 24 days, one passage of the primary culture may be performed preferably between 8 and 17 days, yet more preferably between 12 and 16 days, e.g., most preferably at day 14.

The inventors observed that contacting BMSC with a growth factor, esp. with FGF-2, and human serum or plasma for about 12-16 days may be preferable, as at the end of this period the cells show phenotype closest to osteoblasts. Thereafter, the cells appear to undergo at least partial dedifferentiation, as evidenced by changing morphology, lower ALP and higher levels of differentiation factors. Nevertheless, the above period may be advantageously extended to about 18 to 24 days in order to obtain more resulting osteogenic lineage cells, without a yet substantial dedifferentiation of the cells. Although further prolongation of these periods may be possible, potentially involving further passages, the inventors hypothesize that such prolonged presence of a growth factor, esp. FGF-2, might cause further, unwanted dedifferentiation of the cells. Therefore, the above cited shorter time periods are preferred.

In an embodiment, any medium capable of supporting the growth of fibroblasts in cell culture may be used in the present method. Media formulations that will support the growth of fibroblasts include, but are not limited to, Minimum Essential Medium (MEM), Dulbecco's Modified Eagle's Medium (DMEM), alpha modified Minimum Essential Medium (alpha-MEM), Basal Medium Essential (BME), BGJb, F-12 Nutrient Mixture (Ham), and the like, which are commercially available (e.g., Invitrogen, Carlsbad, Calif.). A particularly suitable medium for use in the present method may be alpha-MEM, IMDM, X-Vivo-10, X-Vivo 20 serum free medium (clinical grade), available from Invitrogen or Cambrex (New Jersey). Such liquid culture media contain ingredients necessary for mammal cell development, which are known per se. For example, these ingredients include inorganic salts (in particular Na, K, Mg, Ca, and possibly Cu, Fe, and Zn), amino acids, vitamins, and sources of carbon (e.g. glucose), etc. Typically, 5-20% of a serum component, e.g., Fetal Calf Serum (FCS), may need to be added to the above media in order to support the growth of fibroblasts. However, a defined serum-free medium could be used if the factors in FCS necessary for fibroblast growth were identified and provided in the growth medium. Advantageously, in the present method, this serum component may by represented by the human plasma or serum with which BMSC are contacted, such that no further serum component is added to the medium. The media may further contain one or more compounds of interest, including, but not limited to, sodium bicarbonate, antibiotic and/or antimycotic components, such as, penicillin, streptomycin and/or amphotericin, etc.

In a preferred embodiment, BMSC are not contacted with any component obtained from a non-human animal, in particular non-human mammal. If osteoprogenitors, osteoblasts or osteoblast phenotype cells obtained from BMSC are to be administered to a human subject, the absence of contact between the BMSC and components obtained from non-human animals ensures optimal acceptance of the cells by the subject and avoids accidental transmission of infectious agents thereto. The latter concern becomes increasingly important due to the appearance of prion diseases, e.g., BSE, which can be transmitted from animals to humans.

In a particular embodiment, BMSC are not contacted with any serum component derived from a non-human animal. For example, media used to culture and differentiate BMSC in the present method may not contain any serum component from a non-human animal. As noted above, addition of, e.g., FCS to cell culture media is commonplace in the art to sustain cell culture growth. Hence, media used to culture and differentiate BMSC in the present method may not include any FCS or other non-human animal serum components. The inventors realised that when BMSC are not contacted with any serum component from a non-human animal, this generates advantageous conditions for obtaining osteoblasts and osteoblast phenotype cells from the BMSC.

In another embodiment, the medium in which BMSC are cultured, does not contain any antibiotic or antimycotic components. Absence of these components allows to more readily discern possible contamination of the culture. If the osteoblasts or osteoblast phenotype cells obtained from the BMSC are to be administered to a human subject, this avoids introducing pathogenic microorganisms to the subject.

In an embodiment, the medium does not contain components which are commonly used in the art to induce osteogenic differentiation, such as, a glucocorticoid (e.g., dexamethasone), ascorbic acid-2-phosphate and/or beta-glycerolphosphate.

Hence, taking into account the above preferred features, in exemplary embodiments, the method for obtaining osteoprogenitors, osteoblasts or osteoblast phenotype cells, or a cell population comprising such (and optionally further comprising other cell types, e.g., endothelial cells or progenitors) in vitro or ex vivo comprises the steps:

(a) recovering cells from a biological sample of a human subject comprising BMSC, preferably a sample of bone marrow;
(b) optionally, isolating mono-nucleated cells from the cells recovered in (a), e.g., using suitable density gradient centrifugation or other methods;
(c) adding cells of (a) or, preferably, (b) to a medium comprising human plasma or serum and a growth factor or a biologically active variant or derivative thereof, and culturing the cell-medium mixture, such as to allow for adherence of cells to a substrate surface, e.g., glass or plastic surface, e.g., of a culture vessel;
(d) removing non-adherent matter and further culturing adherent cells in the medium as defined in (c), such as to allow for obtaining osteoprogenitors, osteoblasts or osteoblast-like cells, or a cell population comprising such.

In a preferred embodiment, the method may further comprise collecting the cells or cell population obtained in (d), preferably at between 12 and 16 days, e.g., at day 14.

In another preferred embodiment, the method may comprise passaging the cells or cell population of (d) between about days 12 and 16 and collecting the so-cultured cells or cell population between about days 18 and 24.

In a preferred embodiment, the culture vessel may provide for a plastic surface to enable cell adherence. In another embodiment, the surface may be a glass surface. In yet another embodiment, the surface may be coated with an appropriate material conducive to growth of the cells, e.g., Matrigel(R), laminin or collagen.

The term "isolating" with reference to a particular component denotes separating that component from at least one other component of a composition from which the former component is being isolated. Hence, isolating BMSC involves separating BMSC from at least one other component of a composition comprising BMSC. Isolating BMSC also involves increasing the proportion of BMSC in a composition relative to other components, in particular to other cellular components, compared to a composition from which the BMSC are being isolated. For example, isolating BMSC from a biological sample denotes separating BMSC from other components, in particular cellular components, of the sample.

The term "isolated" as used herein in relation to any cell population also implies that such cell population does not form part of an animal or human body.

In an embodiment, the cells of (a) or (b) may be plated for culturing at between 1 and $1\times10^6$ cells/mm$^2$, e.g., between 1 and $5\times10^5$ cells/mm$^2$, between 1 and $1.5\times10^5$ cells/mm$^2$, e.g., between $1\times10^3$ and $5\times10^5$ cells/mm$^2$, preferably between $1\times10^4$ and $5\times10^5$ cells/mm$^2$, e.g., between $1\times10^4$ and $1\times10^5$ cells/mm$^2$, or between $5\times10^4$ and $5\times10^5$ cells/mm$^2$, or between $5\times10^4$ and $1\times10^5$ cells/mm$^2$, e.g., about $1\times10^4$, $2\times10^4$, $3\times10^4$, $4\times10^4$, $5\times10^4$, $6\times10^4$, $7\times10^4$, $8\times10^4$, $9\times10^4$, or $1\times10^5$ cells/mm$^2$.

In preferred embodiments, the said removing non-adherent matter in (d) is carried out after between 1 to 8 days, e.g., 2 to 6 days, preferably between 1 and 4 days, more preferably at about 4 days, e.g., at 4 days, and even more preferably at day 1, 2 or 3, yet more preferably at day 1 or 2.

Further, in preferred embodiments, the said further culturing of adherent cells in (d) may be performed for between 5 and 30 days, e.g., for about 10 to 25 days, more preferably about 18 to 22 days, yet more preferably between 18 and 24 days, e.g., 18, 19, 20, 21, 22, 23 or 24 days.

Further in preferred embodiments, the said further culturing of adherent cells in (d) may involve one or more than one, e.g., 2 or 3 passages of the cells, preferably 1 or 2, more preferably 1 passage. Preferably, it may involve a passage at about 10-18 days, e.g., at about 12 to 16 days, e.g., at 14 days, following step (c).

In a preferred embodiment, such passage may be at a constant time in order to standardise the culturing procedure, e.g., at about 14 days, e.g., at 14 days of culture.

Preferably, the cells may be, after passaging, re-plated for further culturing in (d) at between 1 and $1\times10^6$ cells/mm$^2$, e.g., at between $1\times10^2$ and $1\times10^5$ cells/mm$^2$, at between $1\times10^3$ and $1\times10^5$ cells/mm$^2$, preferably between $5\times10^3$ and $5\times10^4$ cells/mm$^2$, e.g. about $5\times10^3$, $6\times10^3$, $7\times10^3$, $8\times10^3$, $9\times10^3$, $1\times10^4$, $2\times10^4$, $3\times10^4$, $4\times10^4$, or $5\times10^4$ cells/mm$^2$, more preferably between $8\times10^3$ and $2\times10^4$ cells/mm$^2$, e.g., about $1\times10^4$ cells/mm$^2$.

In an embodiment, the cells may be re-plated at a confluence of at least 5%, or at least 10%, e.g., at least 30% and no more than 90% or no more than 80% or no more than 50%, and preferably between 30 to 80%.

In an embodiment, the step of passaging includes treatment of the cells with a bivalent ion chelator (e.g., EDTA or EGTA) and/or treatment with trypsin. In a preferred embodiment, the step of passaging includes treatment of the cells with a bivalent ion chelator (e.g., EDTA or EGTA) and not with trypsin. This is advantageous, since trypsin may be derived from animal sources and may therefore carry the risk of introducing pathogenic agents.

Further preferred embodiments of the process steps (a) to (d) are as described above.

As explained above, the methods of the invention, and preferred embodiments thereof, yield osteoprogenitors, osteoblasts or osteoblast phenotype cells, as well as cell populations comprising such, which show superior characteristics, such as, e.g., fast proliferation, rapid mineralization, and substantially absent potential to differentiate towards adipocytes or chondrocytes. The inventors have also realised that these cells and cell populations perform superiorly when implanted in patient bone tissue. Given such surprising characteristics of cells and cell populations obtained by the methods of the invention, these cells and populations are in itself a valuable contribution to the art. Moreover, as further explained in the following section and corroborated by the experimental data, the methods of the invention provide new types of osteogenic cells, as evidenced by new and unexpected combinations of markers on these cells, as well as new cell populations particularly suited for bone therapy.

Hence, it will be appreciated by a skilled person that when BMSC are treated according to the invention to obtain osteoprogenitors, osteoblasts or osteoblast phenotype cells, a cell population is obtained comprised mainly of osteoblasts or osteoblast phenotype cells. However, due to, e.g., fluctuations in cellular responses, the cell population may comprise a minor proportion of cells which are not osteoprogenitors, osteoblasts or osteoblast phenotype cells.

Accordingly, in a related aspect, the invention provides human osteoprogenitors, osteoblasts or osteoblast phenotype cells obtainable or directly obtained using the methods of the invention as described above.

In an embodiment, the invention provides an isolated cell population comprising osteoprogenitors, osteoblasts or osteoblast phenotype cells, said population obtainable or directly obtained using the methods of the invention as described above. For example, such cell population may comprise at least 60%, e.g., at least 65%, preferably at least 70%, e.g., at least 75%, more preferably at least 80%, e.g., 85%, even more preferably at least 90%, e.g., 95% or even at least 96%, at least 97%, at least 98% or at least 99% of osteoprogenitors, osteoblasts or osteoblast phenotype cells.

In a preferred embodiment, the cell population may comprise one or more cell types other than the said osteoprogenitors, osteoblasts or osteoblast phenotype cells. For example, the population may comprise less than 50%, e.g., less than 40%, preferably less than 30%, e.g., less than 20%, more preferably less than 15% or less than 10%, e.g., less than 7%, less than 5% or less than 2% of cell types other than the said osteoprogenitors, osteoblasts or osteoblast phenotype cells.

The actual phenotype of the remaining cells in the cell mixture may be of importance, since rapid proliferation and differentiation of osteoblasts might be at least in part dependent upon endogenous production of substances effecting osteoblasts, e.g., growth factors and/or differentiating factors, by the remaining cells in the mixture. In this respect, it may be interesting that bone development and remodelling is known to be at least in part dependent upon complex interactions between bone-forming osteoblasts and other cells present within the bone microenvironment, particularly endothelial cells, which may be important members of a complex interactive communication network in bone. Cell cooperation between human osteoprogenitor cells and endothelial cells has been previously demonstrated (Guillotin et al. 2004. Cell Physiol Biochem 14(4-6): 325-32). In addition, the presence of endothelial cells may give rise to in situ formations of vessels or capillaries which will irrigate the newly formed bone tissue. The present inventors have found that such remaining cells in the present cell mixture may be endothelial-like and may, in terms of specific markers, be positive for the marker CD133 and/or CD34, and potentially negative for the marker CD45; and in particular and preferably, positive for at least any one, two or all of vWF, VEGF and CD133; and optionally also positive for CD34.

Accordingly, in a further preferred embodiment, the cell population may comprise endothelial cells or progenitors. In a further embodiment, the cell population may comprise osteoprogenitors, osteoblasts or osteoblast phenotype cells and endothelial cells or progenitors.

In another aspect, the invention relates to human osteoprogenitors, osteoblasts or osteoblast phenotype cells obtainable or directly obtained using the methods of the invention as described above, for use in therapy and/or for the manufacture of a medicament for the treatment of bone-related disorders.

In an embodiment, the invention relates to an isolated cell population comprising osteoprogenitors, osteoblasts or osteoblast phenotype cells, said population obtainable or directly obtained using the methods of the invention as described above, for use in therapy and/or for the manufacture of a medicament for the treatment of bone-related disorders.

In an aspect, osteoprogenitors, osteoblasts or osteoblast phenotype cells obtainable by or directly obtained by methods of the present invention, or an isolated cell population comprising osteoprogenitors, osteoblast or osteoblast phenotype cells, said population obtainable or directly obtained using the methods of the invention as described above, may be administered at a site of bone lesion, e.g., surgery or fracture.

In another aspect, the invention provides a method for preventing and/or treating bone disease, comprising administration of osteoprogenitors, osteoblasts or osteoblast phenotype cells obtainable by or directly obtained by methods of the present invention, or of an isolated cell population comprising osteoprogenitors, osteoblast or osteoblast phenotype cells, said population obtainable or directly obtained using the methods of the invention as described above, to a subject in need of such treatment.

In an aspect, the invention relates to a method for preventing and/or treating bone disease, comprising:
(a) obtaining a biological sample comprising BMSC from a subject in need of such treatment;
(b) obtaining osteoprogenitors, osteoblasts or osteoblast phenotype cells, or obtaining an isolated cell population comprising osteoblast or osteoblast phenotype cells, from the BMSC in vitro or ex vivo according to methods of the invention; and
(c) administering the so-obtained osteoprogenitors, osteoblasts or osteoblast phenotype cells or the said cell population comprising such to the subject.

In a preferred embodiment, the step (b) may involve methods of the present invention using autologous human plasma or serum, and more preferably devoid of non-human animal components, e.g., serum components. Such condition may be referred herein as "pure autologous" conditions of obtaining the osteoblasts or osteoblast phenotype cells of the invention.

In a further aspect, the invention relates to a pharmaceutical composition comprising osteoprogenitors, osteoblasts or osteoblast phenotype cells obtainable or directly obtained by methods of the present invention, or comprising an isolated cell population comprising osteoprogenitors, osteoblast or osteoblast phenotype cells, said population obtainable or directly obtained using the methods of the invention as described above, and suitable for administration at a site of bone lesion.

2. Cells and Populations of the Invention

As explained in the Summary section, further study of the cells and cell populations resulting from the methods of the invention allowed the inventors to define new osteoprogenitor, osteoblast or osteoblast phenotype cell types, as well as specific cell populations comprising such, which underlie the advantageous properties observed upon use in bone therapy.

In particular, in an aspect the invention provides osteoprogenitors, osteoblasts or osteoblast phenotype cells (herein, "OOP-1 cells"), preferably of human origin, characterised in that they co-express (1) at least one osteoblast marker chosen from alkaline phosphatase (ALP), more specifically ALP of the bone-liver-kidney type, procollagen type 1 amino-terminal propeptide (P1NP) and bone sialoprotein (BSP) with (2) at least one stem cell/immature osteoprogenitor marker chosen from CD63 and CD166.

Hence, in exemplary embodiments (a) to (u), the osteoprogenitor, osteoblast or osteoblast phenotype (OOP-1) cells co-express: (a) at least ALP and CD63, (b) at least P1NP and CD63, (c) at least BSP and CD63, (d) at least ALP, P1NP and CD63, (e) at least ALP, BSP and CD63, (f) at least P1NP, BSP and CD63, (g) at least ALP, P1NP, BSP and CD63, (h) at least ALP and CD166, (i) at least P1NP and CD166, (j) at least BSP and CD166, (k) at least ALP, P1NP and CD166, (l) at least ALP, BSP and CD166, (m) at least P1NP, BSP and CD166, (n) at least ALP, P1NP, BSP and CD166, (o) at least ALP, CD63 and CD166, (p) at least P1NP, CD63 and CD166, (q) at least BSP, CD63 and CD166, (r) at least ALP, P1NP, CD63 and CD166, (s) at least ALP, BSP, CD63 and CD166, (t) at least P1NP, BSP, CD63 and CD166, or (u) at least ALP, P1NP, BSP, CD63 and CD166.

In a preferred embodiment (v), the osteoprogenitor, osteoblast or osteoblast phenotype (OOP-1) cells, in particular as defined in any of the above embodiments (a) to (u), are negative for osteocalcin (OCN).

In a further preferred embodiment (w), the osteoprogenitor, osteoblast or osteoblast phenotype (OOP-1) cells, in particular as defined in any of the above embodiments (a) to (v), are positive for CD34.

In a further preferred embodiment (x), the osteoprogenitor, osteoblast or osteoblast phenotype (OOP-1) cells, in particular as defined in any of the above embodiments (a) to (v), are negative for CD34.

In a further preferred embodiment (y), the osteoprogenitor, osteoblast or osteoblast phenotype (OOP-1) cells, in particular as defined in any of the above embodiments (a) to (x), are also positive for any one, two or all three of CD90, CD73 and CD105.

In a further preferred embodiment (z), the osteoprogenitor, osteoblast or osteoblast phenotype (OOP-1) cells, in particular as defined in any of the above embodiments (a) to (y), are negative for any one, two or all three of CD45, CD19 and CD14.

In a further preferred embodiment (ab), the osteoprogenitor, osteoblast or osteoblast phenotype (OOP-1) cells, in particular as defined in any of the above embodiments (a) to (z), are negative for CD133.

In a further preferred embodiment (ac), the osteoprogenitor, osteoblast or osteoblast phenotype (OOP-1) cells, in particular as defined in any of the above embodiments (a) to (ab), show evidence of ability to mineralize the external surroundings, or synthesize calcium-containing extracellular matrix, when exposed to osteogenic medium (Jaiswal et al. 1997. J Cell Biochem 64: 295-312). The amount of mineralization after 1 week (measured by the total proportion of Red Alizarin stained surface in mineralization medium, as known in the art) may be at least 40%, preferably at least 45%, more preferably at least 50%, even more preferably at least 55%, and most preferably at least 60%, such as, at least 65%, at least 70%, at least 80%, at least 85%, at least 90% or at least 95% or even 100%. Advantageously, mineralization by these cells is much faster than by classical BMSC, where the above levels can be achieved only after 3 to 4 weeks in osteogenic medium.

Interestingly, the doubling time of the above osteoprogenitors, osteoblasts or osteoblast phenotype cells of the invention in the mineralization medium may be between 1 and 3 days, e.g., about 2 days. This is considerably faster than the doubling time of classical osteoblasts in these conditions, which is about 6-7 days.

In a still further preferred embodiment (ad), the osteoprogenitor, osteoblast or osteoblast phenotype (OOP-1) cells, in particular as defined in any of the above embodiments (a) to (ac), substantially do not differentiate towards any one of, and preferably towards neither of cells of adipocytic lineage (e.g., adipocytes) or chondrocytic lineage (e.g., chondrocytes). The absence of differentiation towards these cell lineages may be tested using standard differentiation inducing conditions established in the art (e.g., see Pittenger et al. 1999. Science 284: 143-7), and assaying methods (e.g., when induced, adipocytes typically stain with oil red O showing lipid accumulation; chondrocytes typically stain with alcian blue or safranin O).

Substantially lacking propensity towards adipogenic or chondrogenic differentiation may typically mean that less than 50% of the tested cells, e.g., tested OOP-1 cells, preferably less than 40%, e.g., less than 30%, more preferably less than 20%, even more preferably less than 10%, and still more preferably less than 5%, e.g., less than 4%, less than 3%, less than 2%, or less than 1% or even less than 0.1%, would show signs of adipogenic or chondrogenic differentiation when applied to the respective test.

In a further aspect the invention provides osteoprogenitor, osteoblast or osteoblast phenotype cells (herein, "OOP-2 cells"), preferably of human origin, characterised in that they co-express (1) at least one osteoblast marker chosen from alkaline phosphatase (ALP), more specifically ALP of the bone-liver-kidney type, procollagen type 1 amino-terminal propeptide (P1NP) and bone sialoprotein (BSP) with (2) the hematopoietic/endothelial progenitor marker CD34.

Hence, in exemplary embodiments (a') to (g'), the osteoprogenitor, osteoblast or osteoblast phenotype (OOP-2) cells co-express: (a') at least ALP and CD34, (b') at least P1NP and CD34, (c') at least BSP and CD34, (d') at least ALP, P1NP and CD34, (e') at least ALP, BSP and CD34, (f') at least P1NP, BSP and CD34, or (g') at least ALP, P1NP, BSP and CD34.

In a preferred embodiment (h'), the osteoprogenitor, osteoblast or osteoblast phenotype (OOP-2) cells, in particular as defined in any of the above embodiments (a') to (g'), are negative for osteocalcin (OCN).

In a further preferred embodiment (i'), the osteoprogenitor, osteoblast or osteoblast phenotype (OOP-2) cells, in particular as defined in any of the above embodiments (a') to (g'), are positive for CD63.

In a further preferred embodiment (j'), the osteoprogenitor, osteoblast or osteoblast phenotype (OOP-2) cells, in particular as defined in any of the above embodiments (a') to (i'), are positive for CD166.

In a further preferred embodiment (k'), the osteoprogenitor, osteoblast or osteoblast phenotype (OOP-2) cells, in particular as defined in any of the above embodiments (a') to (j'), are also positive for any one, two or all three of CD90, CD73 and CD105.

In a further preferred embodiment (l'), the osteoprogenitor, osteoblast or osteoblast phenotype (OOP-2) cells, in particular as defined in any of the above embodiments (a') to (k'), are negative for any one, two or all three of CD45, CD19 and CD14.

In a further preferred embodiment (m'), the osteoprogenitor, osteoblast or osteoblast phenotype (OOP-2) cells, in particular as defined in any of the above embodiments (a') to (l'), are negative for CD133.

In a further preferred embodiment (n'), the osteoprogenitor, osteoblast or osteoblast phenotype (OOP-2) cells, in particular as defined in any of the above embodiments (a') to (m'), show evidence of ability to mineralize the external surroundings, or synthesize calcium-containing extracellular matrix, when exposed to osteogenic medium (Jaiswal et al. 1997). The amount of mineralization after 1 week (measured by the total proportion of Red Alizarin stained surface in mineralization medium, as known in the art) may be at least 40%, preferably at least 45%, more preferably at least 50%, even more preferably at least 55%, and most preferably at least 60%, such as, at least 65%, at least 70%, at least 80%, at least 85%, at least 90% or at least 95% or even 100%. Advantageously, mineralization by these cells is much faster than by classical BMSC, where the above levels can be achieved only after 3 to 4 weeks in osteogenic medium.

Interestingly, the doubling time of the above osteoprogenitors, osteoblasts or osteoblast phenotype cells of the invention in the mineralization medium may be between 1 and 3 days, e.g., about 2 days. This is considerably faster than the doubling time of classical osteoblasts in these conditions, which is about 6-7 days.

In a still further preferred embodiment (o'), the osteoprogenitor, osteoblast or osteoblast phenotype (OOP-2) cells, in particular as defined in any of the above embodiments (a') to (n'), substantially do not differentiate towards any one of, and preferably towards neither of cells of adipocytic lineage (e.g., adipocytes) or chondrocytic lineage (e.g., chondrocytes).

Wherein a cell is said to be positive for a particular marker, this means that a skilled person will conclude the presence or evidence of a distinct signal, e.g., antibody-detectable or detection possible by reverse transcription polymerase chain reaction, for that marker when carrying out the appropriate measurement, compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of cell-specific markers can be detected using any suitable immunological technique known in the art, such as flow cytometry, immuno-cytochemistry or affinity adsorption, Western blot analysis, ELISA, etc., or by any suitable technique of measuring the quantity of the marker mRNA, e.g., Northern blot, semi-quantitative or quantitative RT-PCR, etc.

In embodiments, the above osteoprogenitors, osteoblasts or osteoblast phenotype cells, when said to be ALP positive, will be ALP positive as determined by FACS. In embodiments, the ALP positive cells will contain at least 300 mU ALP per 1 mg total cellular protein, preferably at least 400 mU ALP per 1 mg total cellular protein, more preferably at least 450 mU ALP per 1 mg total cellular protein, e.g., at least 500 mU, at least 600 mU, at least 700 mU, at least 800 mU, at least 900 mU or at least 1 U of ALP per 1 mg total cellular protein. For example, the ALP activity may be between 400 and 1500 mU per 1 mg total cellular protein, e.g., between 450 and 1500 mU, between 500 and 1500 mU, between 550 and 1500 mU or between 600 and 1500 mU per 1 mg total cellular protein, and may be typically between 400 and 800 mU per 1 mg total cellular protein, e.g., about 500 mU, about 550 mU, about 600 mU, about 650 mU, about 700 mU, about 750 mU or about 800 mU per 1 mg of cellular protein. The above ALP activity may be present in combination with one or more other characteristics (a) to (h) as defined above.

In embodiments, osteoprogenitors, osteoblasts or osteoblast phenotype cells of the invention, when said to be P1NP positive, will produce the procollagen type 1 amino-terminal propeptide (P1NP) in the culture media in the following amounts of (P1NP is expressed in ng per ml of medium per $10^6$ cells): at least 0,4 ng, preferably at least 0,5, more preferably at least 1,0, even more preferably at least 1,2 and most preferably at least 1,5, e.g., at least 1,6, at least 1,7, at least 1,8 or at least 2. For example, P1NP may be between 0,4 and 3,5, e.g. between 0,5 and 3,5, between 0,8 and 3,5, between 1,0 and 3,5, between 1,2 and 3,5, between 1,5 and 3,5, between 1,8 and 3,5, between 2,0 and 3,5, between 2,2 and 3,5, between 2,5 and 3,5, between 2,8 and 3,5 or between 3,0 and 3,5; e.g., about 1,5, about 1,6, about 1,7, about 1,8, about 1,9 or about 2,0. The above P1NP production may be present in combination with one or more other characteristics (a) to (h) as defined above.

In other embodiments, osteoprogenitors, osteoblasts or osteoblast phenotype cells of the invention, when said to be BSP positive, may contain a moderate to high quantity of bone sialoprotein. When measured by quantitative methods (e.g., quantitative RT-PCR), the signal generated in osteoprogenitors, osteoblasts or osteoblast phenotype cells of the invention may be at least 2-fold higher than that generated by control cells (e.g., any other non-osteogenic cells), and may be, preferably, at least 4-fold, at least 10-fold, and more preferably at least 20-fold, at least 30-fold, at least 40-fold or at least 50-fold higher. The above bone sialoprotein production may be present in combination with one or more other characteristics (a) to (h) as defined above.

Generally, the above recited CD and other markers are known in the art and ways of and reagents for their detection in cells are available to a skilled one.

In a further aspect, the invention encompasses cell populations comprising the above osteoprogenitor, osteoblast or osteoblast phenotype cells, e.g., comprising the OOP-1 and/or OOP-2 cell types as above. Preferably, such cell population may comprise at least 10%, preferably at least 30%, more preferably at least 50%, e.g., at least 60%, yet more preferably at least 70%, e.g., at least 80%, and even more preferably at least 90%, e.g., at least 95%, or even at least 96%, at least 97%, at least 98% or at least 99% of the OOP-1 and/or OOP-2 cell types.

For example, of the total fraction of osteoprogenitor, osteoblast or osteoblast phenotype cells, OOP-1 cells may constitute at least 5%, or at least 10%, or at least 20%, or at least 30%, or at least 40%, or at least 50%, or at least 60%, or at least 70%, or at least 80% or at least 90% or at least 95% or even 100%, while OOP-2 may substantially constitute remaining cells of the said fraction.

In preferred embodiments, the cell population may comprise less than 50%, preferably less than 40%, even more preferably less than 30%, yet more preferably less than 20% and still more preferably less than 10%, e.g., less than 7%, less than 5% or less than 2% of cell types other than the above osteoprogenitors, osteoblasts or osteoblast phenotype cells, esp. OOP-1 and/or OOP-2 cell types.

In a preferred embodiment, the said cell population may comprise endothelial cells or progenitors thereof.

Preferably, such endothelial cells or progenitors may express at least one, e.g., at least two, or at least all three, of von Willebrand factor (vWF), VEGF and CD133.

Accordingly, in embodiments (a") to (g"), the said endothelial cells express: (a") at least vWF, (b") at least VEGF, (c") at least CD133, (d") at least vWF and VEGF, (e") at least vWF and CD133, (f") at least VEGF and CD133, or (g") at least vWF, VEGF and CD133.

In a further embodiment (h"), the said endothelial cells, esp. of embodiments (a") to (g") as above, further express CD34.

Accordingly, in an embodiment, the cell population comprises (A) osteoprogenitors, osteoblasts or osteoblast phenotype cells, especially the OOP-1 and/or OOP-2 cells as defined above, and further comprises (B) endothelial cells or progenitors as defined above.

In an embodiment, the osteogenic cells under (A) and the endothelial cells under (B) together constitute at least 50%, e.g., at least 60%, preferably at least 70%, e.g., at least 80%, more preferably at least 90%, even more preferably at least 95%, and most preferably at least 96%, e.g., at least 97%, at least 98%, or at least 99%, or even 100% of cells forming the said cell population.

Of this (A+B) fraction, the osteogenic cells under (A) preferably constitute at least 50%, e.g., at least 60%, more preferably at least 70%, e.g., at least 80%, and even more preferably at least 90%, e.g., at least 95%, at least 96%, at least 97%, at least 98%, or even at least 99%, in preferred examples, between 90% and 99%, between 90% and 95%, or between 95% and 99%.

Consequently, of this (A+B) fraction, the endothelial cells under (B) preferably constitute less than 50%, e.g., less than 40%, more preferably less than 30%, e.g., less than 20%, and even more preferably less than 10%, e.g., less than 5%, less than 4%, less than 3%, less than 2%, or even less than 1%, in preferred examples, between 1% and 10%, between 5% and 10%, or between 1% and 5%.

It shall be appreciated that the herein disclosed cell types and cell populations can be advantageously arrived at using the differentiation methods of the invention. Such methods may be optionally supplemented by further separation or isolation of particular cell types (e.g., using FACS based on the marker profile), and optionally combination of such cell types to form desired populations.

Nevertheless, it is to be understood that the invention defines the cell types and populations by their structural and functional characteristics, i.e., per se, and is not limited to any way of preparation thereof. By means of example and not limitation, osteoprogenitors, osteoblasts or osteoblast phenotype cells as defined above, might be obtained using other conditions of differentiating cells into osteogenic lineage, and selecting, e.g., by FACS, cells having the particular marker profiles as defined herein. Similarly, the endothelial cells might also be generated by applying, e.g., angiogenic factors, or from hematopoietic cells, followed by selection of cells with the desired marker profile.

In further aspects, the invention also relates to particular populations having particular marker profiles.

For example, the invention relates to a cell population ("POP 1") wherein between 70% and 100%, preferably between 80% and 100%, more preferably between 90% and 100%, even more preferably between, 95% and 100%, e.g., up to between 90% and 100% or between 90% and 98%, or between 95% and 98%, are CD105 positive and, preferably, also CD45 negative, CD19 negative, CD14 negative, CD90 positive and CD73 positive.

The invention further relates to population 2 ("POP 2") having the features as POP 1, and further wherein between 70% and 100%, preferably between 80% and 100%, more preferably between 90% and 100%, even more preferably between, 95% and 100% of CD105 positive cells are also ALP positive and/or P1NP positive and/or BSP positive.

The invention further relates to population 3 ("POP 3") having the features as POP 1, and further wherein between 50% and 100%, e.g., between 60% and 100%, preferably between 70% and 100%, e.g., between 80% and 100%, more preferably between 90% and 100%, even more preferably between, 95% and 100% of CD105 positive cells are also CD63 positive and/or CD166 positive.

The invention further relates to population 4 ("POP 4") having the features as POP 2, and further wherein between 50% and 100%, e.g., between 60% and 100%, preferably between 70% and 100%, e.g., between 80% and 100%, more preferably between 90% and 100%, even more preferably between, 95% and 100% of ALP positive and/or P1NP positive and/or BSP positive cells are also CD63 positive and/or CD166 positive.

The invention further relates to population 5 ("POP 5") having the features as any of POP 1 or POP 3, and wherein between 1% and 20%, preferably between 1% and 10%, more preferably between 1% and 5% of cells are vWF positive and/or VEGF positive and/or CD133 positive.

The invention also relates to a population 6 ("POP 6"): wherein between about 50% and about 98%, preferably between about 70% and about 98% and even more preferably between about 80% and about 98%, e.g., between about 90% and about 98% of cells are ALP positive; wherein between about 30% and about 98%, preferably between about 40% and about 98% and even more preferably between about 50% and about 98%, e.g., between about 60% and about 98%, between about 70% and 98%, between about 80% and 98%, or even between about 90% and 98% of cells are CD166 positive; wherein between about 30% and about 98%, preferably between about 40% and about 98% and even more preferably between about 50% and about 98%, e.g., between about 60% and about 98%, between about 70% and 98%, between about 80% and 98%, or even between about 90% and 98% of cells are CD63 positive; wherein between about 0.5% and about 10%, preferably between about 1% and 10%, even more preferably between about 1% and 4% of cells are CD133 positive; wherein between about 0.5% and about 10%, preferably between about 1% and 10%, even more preferably between about 1% and 4% of cells are VEGF positive; and wherein between about 0.5% and about 10%, preferably between about 2% and 10%, even more preferably between about 5% and 10%, e.g., between about 8% and 10% of cells are vWF positive.

In related aspects, the invention relates to the above defined cells or cell populations for use in therapy and/or for the manufacture of a medicament for the treatment of bone-related disorders.

In an aspect, the above defined cells or cell populations may be administered at a site of bone lesion, e.g., surgery or fracture.

In another aspect, the invention provides a method for preventing and/or treating bone disease, comprising administration of the above defined cells or cell populations to a subject in need of such treatment.

In an aspect, the invention relates to a method for preventing and/or treating bone disease, comprising:
(a) obtaining the above defined cells or cell populations, and
(b) administering the so-obtained cells or cell populations to the subject.

In a preferred embodiment, the step (a) may involve methods of the present invention using autologous human plasma or serum, and more preferably devoid of non-human animal components, e.g., serum components. Such condition may be referred herein as "pure autologous" conditions of obtaining the osteoblasts or osteoblast phenotype cells of the invention.

In a further aspect, the invention relates to a pharmaceutical composition comprising cells and cell populations as defined above, and suitable for administration at a site of bone lesion.

3. Further Aspects Relating to Cells and Populations of the Invention

The present aspects relate to osteoprogenitors, osteoblasts or osteoblast phenotype cells and populations comprising such, as obtained or obtainable by methods described in section 1 above; as well as to osteoprogenitors, osteoblast phenotype cells, and cell populations comprising such, per se, as described in section 2 above.

In a further aspect, the invention relates to an arrangement comprising a surgical instrument for administration of a composition at a site of bone lesion and further comprising the pharmaceutical composition comprising the cells or cell populations of the invention as defined above, wherein the arrangement is adapted for administration of the pharmaceutical composition at the site of bone lesion. For example, a suitable surgical instrument may be capable of injecting a liquid composition comprising cells of the present invention at the site of bone lesion.

According to the above aspects, the cells or cell populations of the invention may be introduced into the bone of a human subject at the site of surgery or fracture. Introduction of osteoblasts to bone is useful in the treatment of bone fractures and bone-related disorders.

As noted, preferably, the osteoblasts are obtained from BMSC of the subject into which the differentiated osteoblasts may be introduced. However, BMSC may also be isolated from an organism of the same or different species as the subject. The subject may be any organism having bone tissue. Preferably the subject is mammalian, most preferably the subject is human.

The BMSC cells or the cells or cell populations of the invention may be stably or transiently transformed with a nucleic acid of interest prior to introduction into the bone lesion, e.g., a surgery or fracture site, of the subject. Nucleic acid sequences of interest include, but are not limited to those encoding gene products that enhance the growth, differentiation and/or mineralization of osteoblasts. For example, an expression system for BMP-4, can be introduced into the BMSC in a stable or transient fashion for the purpose of treating non-healing fractures or osteoporosis. Methods of transformation of BMSC and osteoblasts are known to those skilled in the art, as are methods for introducing osteoblasts into a bone at the site of bone lesion, e.g., surgery or fracture.

The cells or cell populations of the invention may be introduced alone or in admixture with further components useful in the repair of bone wounds and defects. Such compositions include, but are not limited to bone morphogenetic proteins, hydroxyapatite/tricalcium phosphate particles (HA/TCP), gelatin, poly-lactic acid, poly-lactic glycolic acid, hyaluronic acid, chitosan, poly-L-lysine, and collagen. For example, osteoblasts differentiated from adipose stromal cells may be combined with Demineralized Bone Matrix (DBM) or other matrices to make the composite osteogenic (bone forming in it own right) as well as osteo-inductive. Similar methods using autologous bone marrow cells with allogeneic DBM have yielded good results (Connolly et al. 1995. Clin Orthop 313: 8-18).

When cells or cell populations of the invention are introduced alone or in admixture with further components, the composition (e.g., pharmaceutical composition) may contain further components ensuring the viability of such cells, e.g., osteoprogenitors, osteoblasts or osteoblast phenotype cells therein. In particular, the cells or cell populations can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the device used for administration. For example, the composition may comprise a suitable buffer system to suitable pH, e.g., near neutral pH (e.g., phosphate or carbonate buffer system), and may comprise sufficient salt to ensure iso-osmotic conditions for the cells or cell populations, i.e., preventing osmotic stress. For example, suitable solution for these purposes may be phosphate-buffered saline (PBS) as known in the art. Further, the composition may comprise a carrier protein, e.g., albumin, which may increase the viability of the cells. Preferably, to ensure exclusion of non-human animal material, the albumin may be of human origin (e.g., isolated from human material or produced recombinantly). Suitable concentrations of albumin are generally known.

The cells or cell populations can be administered in a manner that permits them to graft or migrate to the intended tissue site and reconstitute or regenerate the functionally deficient area. Administration of the composition will depend on the musculoskeletal site being repaired. For example, osteogenesis can be facilitated in concordance with a surgical procedure remodel tissue or insert a split, or a prosthetic device such as a hip replacement. In other circumstances, invasive surgery will not be required, and the composition can be administered by injection or (for repair of the vertebral column) using a guidable endoscope.

If desired, the cell preparation can further include or be co-administered with a complementary bioactive factor such as a bone morphogenic protein, such as BMP-2 or BMP-4, or any other growth factor. Other potential accompanying components include inorganic sources of calcium or phosphate suitable for assisting bone regeneration (WO 00/07639). If desired, cell preparation can be administered on a carrier matrix or material to provide improved tissue regeneration. For example, the material can be a granular ceramic, or a biopolymer such as gelatin, collagen, osteonectin, fibrinogen, or osteocalcin. Porous matrices can be synthesized according to standard techniques (e.g., Mikos et al., Biomaterials 14:323, 1993; Mikos et al., Polymer 35:1068, 1994; Cook et al., J. Biomed. Mater. Res. 35:513, 1997).

In an embodiment the cell preparation as define above may be administered in a form of liquid composition.

In another embodiment, the cells or cell populations of the invention may be transferred to and/or cultured on suitable substrate to provide for implants. The substrate on which the cells can be applied and cultured can be a metal, such as titanium, cobalt/chromium alloy or stainless steel, a bioactive surface such as a calcium phosphate, polymer surfaces such as polyethylene, and the like. Although less preferred, siliceous material such as glass ceramics, can also be used as a substrate. Most preferred are metals, such as titanium, and calcium phosphates, even though calcium phosphate is not an indispensable component of the substrate. The substrate may be porous or non-porous.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted.

The three-dimensional solid support must be biocompatible so as to enable it to be implanted in a human. It can be of any suitable shape such as a cylinder, a sphere, a plate, or a part of arbitrary shape. Of the materials suitable for the biocompatible three-dimensional solid support, particular mention can be made of calcium carbonate, and in particular aragonite, specifically in the form of coral skeleton, porous ceramics based on alumina, on zirconia, on tricalcium phosphate, and/or hydroxyapatite, imitation coral skeleton obtained by hydrothermal exchange enabling calcium carbonate to be transformed into hydroxyapatite, or else apatite-wollastonite glass ceramics, bioactive glass ceramics such as Bioglass™ glasses.

EXAMPLES

Example 1

Method to Differentiate BMSC into Osteoblasts 30 ml of bone marrow is removed from iliac crest of a human subject and 100 ml of blood is removed from the same subject.

Plasma is prepared from the blood as usual in the art. More specifically, blood supplied with the anti-coagulant heparin is centrifuged at 2000 rpm, 15 min at 20° C., to remove the cellular components, plasma is recovered, heat inactivated at 56° C. for 50 min, cleared by centrifugation at 3000 rpm, 15 min, filtered through a 0.22 µm sterilisation filter, divided into aliquots and stored at −80° C.

Mono-nucleated cells are recovered from the bone marrow sample using Ficoll gradient centrifugation, in particular using Ficoll Paque Plus (Amersham Pharmacia) and centrifugation at 1400 rpm (450 g), 30 min at 20° C.

The cells were recovered, washed in PBS and deposited in culture flasks with medium containing IMDM (clinical grade) serum-free medium (Cambrex), 20% autologous plasma isolated above and 1 ng/ml FGF-b (Peprotech), at $10 \times 10^6$ cells per 175 $cm^2$ culture flask (Corning). At 4 days of culture, the totality of the medium is changed, thereby removing the non-adherent matter. At days 7 and 11, half of the medium is changed. At day 12, 13 or 14, the cells are washed with PBS, detached using EDTA and passaged for further culture in the same medium, at $1 \times 10^6$ cells per 175 $cm^2$ culture flask. At between day 21 and 24 of culture, the cells are harvested as above. For the purposes of transplantation, the cells are re-suspended in sterile PBS containing 5% human albumin. A portion of the cells is used for phenotypic characterisation (example 2).

Example 2

Phenotypic Characterisation of Osteoblasts and Osteoblast-Like Cells Obtained by the Method of Example 1

After 21 days of culture in the Cell Therapy Unit, the cells are harvested for the injection to the patient and for characterization. $20 \times 10^6$ cells are prepared for the injection. The remaining cells are used for phenotypic characterization:
1. Semi-Quantitative Measurement of Bone Sialoprotein by RT-PCR 2

1 to 2 $10^6$ cells are lyzed in a RNA extraction buffer (RLT buffer, RNeasy kit Qiagen) and stored at −80° C. until processed. Total RNA is extracted from the lysates using the RNeasy kit from Qiagen. One µg of total RNA was reverse transcribed using random hexamers and reverse transcriptase. The first strand cDNA product is subjected to reverse transcription polymerase chain reaction (RT-PCR) using oligonucleotide primer pairs for bone sialoprotein (BSP) and a housekeeping gene, β-actin. The RT-PCR products are analyzed by electrophoresis in a 2% agarose gel and visualized for a semi-quantitative measurement of Bone Sialoprotein (BSP) (0=no expression, +=weak expression; ++=moderate expression, +++=high expression).

Result: Bone sialoprotein expression (n=6). Expression of BSP is ++ on average (range from + to ++)

Dosage of Total Procollagen Type1 Amino-Terminal Propeptide (P1NP) in Cultured Media At day 21, 2 ml of the cultured media is stored at −20° C. for the dosage of P1NP. P1NP level is measured by electrochemiluminescence immunoassay (Roche, Elecsys, 1010/2010 modular analytics).

Result: P1NP=21-90 (range) ng/ml of cultured media (n=6)

Alkaline Phosphatase Activity (APA) Measurement $5\ 10^5$-$10^6$ cells are used for the measurements of alkaline phosphatase activity.

Result: Alkaline phosphatase (n=10). APA: 693±126 mU/mg protein (mean±SEM); Range: 274-1472 mU/mg protein Mineralization Capacity At day 14 of the culture, one 6-well plate is seeded for the study of the capacity of mineralization.

At day 21 the media of this plate is changed to MEM +15% FCS+50 μg/ml ascorbic acid +$10^{-8}$ M dexamethason+10 mM β-glycerophosphate (EMEM, BioWhittaker BE12-136F; FCS In Vitrogen; Ascorbic acid Sigma A-4403; Dexamethason Sigma D-4902; β-glycerophosphate Sigma G-9891)

Visualization of mineralization by a Alizarin coloration at day 28: fix the cells in formaldehyde 4% in PBS, rinse with PBS, incubate with Alizarin red 2% pH 4.1 for coloration.

Mineralization is evaluated as percentage of total culture dish surface (n=10)

Specific Examples of the Above Measurements in Patients

| patients | Marrow (ml) | MNC × $10^6$ after Ficoll | MNC × $10^6$ in culture | Harvest primary culture (day 7) ×$10^6$ | Harvest secondary culture (day 21) ×$10^6$ | Cells injected (×$10^6$) | APA (mU/mg protein) | BSP | P1NP ng/ml | Mineralization (% of total surface) |
|---|---|---|---|---|---|---|---|---|---|---|
| N° 1 | 27 | 44.3 | 44.3 | 17.1 | 70.8 | 20 | 640 | ++ | 43 | >65% |
| N° 2 | 32 | 60 | 50 | 12 | 28 | 20 | 773 | ++ | 82 | >65% |
| N° 3 | 31 | 15.6 | 15.6 | 11.5 | 122 | 20 | 274 | + | 26 | >65% |

The cells are washed with 2 ml of PBS and sonicated in distilled water. After centrifugation the supernatants are used for the determination of alkaline phosphatase activity and protein content.

Reagents were prepared as follows. Preparation of Diethanolamine buffer: 1 M, pH 9.8. Stock solution (D 8885-Sigma-Aldrich) is diluted 10 fold in water and adjusted to pH 9,8 with HCl. Preparation of reaction solution: 1M diethanolamine pH 9,8 and 0,5 mM MgCl2 (M 8266 Sigma-Aldrich) solution. Preparation of pNPP substrate: 10 mM of the 4-nitrophenylphosphate disodium salt hexahydrate (N 4645, Sigma-Aldrich) solution in the reaction solution.

APA catalyzes the following reaction:

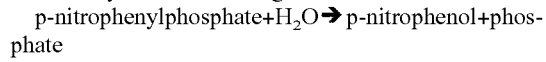

Incubate the substrate solution at 37° C.; 20 μl of supernatant+1000 μl of substrate. Transfer in a spectrophotometric tube at 37° C.; after 2 minutes reading at 405 nm, incubate another 2 minutes and read again, and last reading after another 2 minutes. Calculate the mean of the deltas (differentials) of absorbance and express the delta of absorbance/min Calculation: 1 U=the amount of enzyme to produce one micromole of p-nitrophénol per minute. Coefficient of molar absorption of p-nitrophénol=18450, mmolaire=18,45 μmolaire=0,01845. For a sample of 20 μl: APA (U/L, or mU/ml)=deltaA×1020/0,01845×20.

Quantity of Proteins.

Coomassie solution is prepared as follows: 100 mg blue of Coomassie (Merck 1.15444)+50 ml ethanol 95%+100 ml $H_3PO_4$ 85%+$H_2O$ to 1 L, homogenize and filter. Solution containing bovine albumin 1 mg/ml is prepared as follows: 10 to 50 μl de BSA (1 mg/ml)+$H_2O$ to 1 ml.

Samples are prepared as follows: 200 μl supernatant+800 μl $H_2O$ or 500 μl supernatant+500 μl $H_2O$. Add 2 ml of the Coomassie solution and vortex. After 5 min, measure OD at 595 nm. Express the protein in mg/ml.

For each sample the APA level is reported to the total concentration of protein (mU/mg protein).

Figure 2:
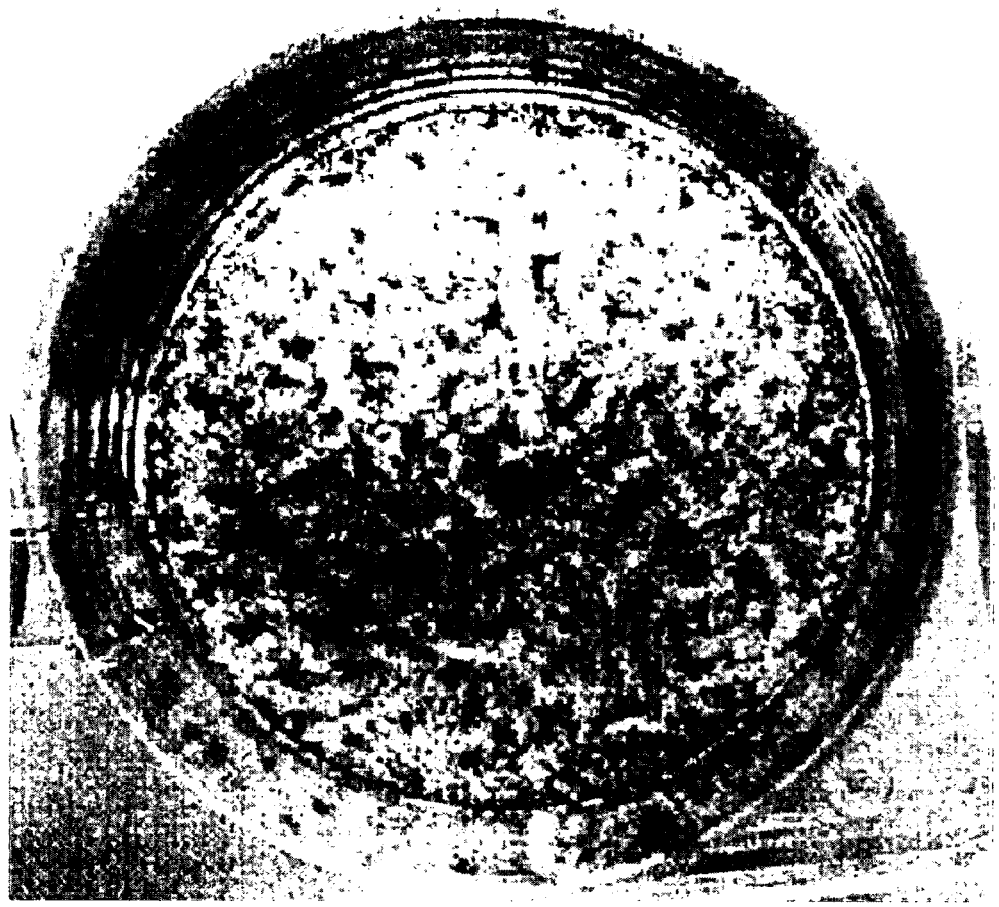
FIG. 2 shows mineralization by the cells/populations of the invention.

In further experiments, mineralization capacity as high as 75% or more at 1 week was even observed (see FIG. 2).

Profiling of Markers

Marker expression was followed as above and/or by antibody staining and flow cytometry of the cells. These experiments yielded the following picture of marker expression in the harvested cells.

The total population was >95% (or even >99%) CD45−, CD19−, CD14−, CD90+, CD73+, CD105+. 90-95% of all cells could be characterised as osteoprogenitor or osteoblast phenotype. Of these 100% was ALP+, 50-100% was CD166+ and 65-100% was CD63+. These cells were also P1NP and BSP positive. 35% to 65% of these cells were CD34+. (In the total population, this corresponded to 80-98% ALP+ cells, 40-98% CD166+ cells and 60-98% CD63+ cells.)

In addition, the total population contained endothelial cells or progenitors thereof in an estimated quantity of 5-10% of total cells. Of these cells, 50-75% were positive for vWF (Von Willebrand Factor), 25-50% were VEGF+ and 25-50% were CD133+. About 50% cells co-expressed CD133 and VEGF. All these cells were CD34+. (In total population, this represented 1-4% CD133 positive cells, 1-4% VEGF positive cells and about 5-8% vWF positive cells.)

Further marker profiling allowed the inventors to define the present cell types as also detailed elsewhere in this disclosure.

Example 3

Transplantation of the Cells of Example 2 to Patients

In one example, a patient with stage 2 osteonecrosis of the femoral head was treated by osteoblasts implantation into the hip necrotic zone, according to a method previously described by Gangji et al. 2005 (Expert Opin Biol Ther 5(4): 437-42; J Bone Joint Surg Am 87 Suppl 1:106-12)

At baseline, the patient had a pain score (visual analogue score—VAS) of 38 mm (out of a total score of 100), and hip functional scores of WOMAC at 43 (out of a total score of 96) and of Lesquesne at 11 (out of a total score of 24).

The patient treated by osteoblast implantation demonstrated a marked improvement in joint symptoms after 3 and 6 months: the VAS score fell to 0 at 3 and 6 months (FIG. 1A), WOMAC fell to 0 at 3 months and at 6 months (FIG. 1B) and the Lequesne index decreased from 11 at baseline to 0 at 3 and at 6 months.

In another example, a patient with stage 2 osteonecrosis of the femoral head was treated by osteoblasts implantation into the hip necrotic zone, according to the same method. At baseline, the patient had a visual analogue pain score of 6 mm and a functional score of Lesquesne at 3.

The patient treated by osteoblast implantation demonstrated a marked improvement in joint symptoms after 3 and 6 months: the VAS score fell to 0 at 3 and 6 months and the Lequesne index fell to 0 at 3 months and at 6 months. In addition, the other hip, which was not implanted by osteoblasts, evolved to final osteonecrosis stage, requiring total hip replacement.

What is claimed is:

1. An isolated cell population comprising:
   (a) human osteoblasts or osteoblast phenotype cells characterised in that they co-express (1) at least one osteoblast marker selected from alkaline phosphatase (ALP) of the bone-liver-kidney type, procollagen type 1 aminoterminal propeptide (PINP) and bone sialoprotein (BSP) with (2) at least one marker selected from CD63 and CD166, and
   (b) endothelial cells or progenitors thereof which are CD34 positive and further express at least one, at least two, or all three, of von Willebrand factor (vWF), VEGF and CD133, said isolated cell population comprising at least 80% of human osteoblasts or osteoblast phenotype cells as defined under (a), and wherein the endothelial cells or progenitors thereof as defined under (b) constitute less than 20% of all cells defined under (a) and (b).

2. The isolated cell population according to claim 1, wherein the human osteoblasts or osteoblast phenotype cells under (a) co-express ALP of the bone-liver-kidney type, P1NP and BSP with at least one of CD63 and CD166.

3. The isolated cell population according to claim 1, wherein one, more than one, or all of the following apply in respect of the human osteoblasts or osteoblast phenotype cells under (a):
   the cells are negative for osteocalcin (OCN);
   the cells are positive for CD34;
   the cells are positive for any one, two or all three of CD90, CD73 and CD105;
   the cells are negative for any one, two or all three of CD45, CD19 and CD 14;
   the cells are negative for CD133.

4. The isolated cell population according to claim 1, wherein the following apply in respect of the human osteoblasts or osteoblast phenotype cells under (a):
   the cells can mineralize the external surroundings, or synthesize calcium-containing extracellular matrix, when exposed to osteogenic medium;
   the cells do not differentiate towards cells of adipocytic lineage nor chondrocytic lineage.

5. An isolated cell population comprising:
   (a) human osteoblasts or osteoblast phenotype cells characterised in that they co-express (1) at least one osteoblast marker selected from alkaline phosphatase (ALP) of the bone-liver-kidney type, procollagen type 1 aminoterminal propeptide (P1NP) and bone sialoprotein (BSP) with (2) the marker CD34, and
   (b) endothelial cells or progenitors thereof which are CD34 positive and further express at least one, at least two, or all three, of von Willebrand factor (vWF), VEGF and CD133, said isolated cell population comprising at least 50% of human osteoblasts or osteoblast phenotype cells as defined under (a), and wherein the endothelial cells or progenitors thereof as defined under (b) constitute less than 20% of all cells defined under (a) and (b).

6. The isolated cell population according to claim 5, wherein the human osteoblasts or osteoblast phenotype cells under (a) co-express ALP of the bone-liver-kidney type, P1NP and BSP with CD34.

7. The isolated cell population according to claim 5, wherein one, more than one, or all of the following apply in respect of the human osteoblasts or osteoblast phenotype cells under (a):
   the cells are negative for osteocalcin (OCN);
   the cells are positive for CD63;
   the cells are positive for CD166;
   the cells are positive for any one, two or all three of CD90, CD73 and CD105;
   the cells are negative for any one, two or all three of CD45, CD19 and CD14;
   the cells are negative for CD133.

8. The isolated cell population according to claim 5, wherein the following apply in respect of the human osteoblasts or osteoblast phenotype cells under (a):
   the cells can mineralize the external surroundings, or synthesize calcium-containing extracellular matrix, when exposed to osteogenic medium;
   the cells do not differentiate towards cells of adipocytic lineage nor chondrocytic lineage.

9. A pharmaceutical composition comprising the cell population as defined in claim 1, and suitable for administration of the said cells or isolated cell population at a site of bone lesion.

10. The pharmaceutical composition according to claim 9 further comprising a carrier matrix or substrate.

11. The isolated cell population according to claim 1, wherein said isolated cell population comprises at least 90% of human osteoblasts or osteoblast phenotype cells as defined under (a).

12. The isolated cell population according to claim 1, wherein said isolated cell population comprises at least 95% of human osteoblasts or osteoblast phenotype cells as defined under (a).

13. The isolated cell population according to claim 5, wherein said isolated cell population comprises at least 90% of human osteoblasts or osteoblast phenotype cells as defined under (a).

14. The isolated cell population according to claim 5, wherein said isolated cell population comprises at least 95% of human osteoblasts or osteoblast phenotype cells as defined under (a).

15. A pharmaceutical composition comprising the cell population as defined in claim 5, and suitable for administration of the said cells or isolated cell population at a site of bone lesion.

16. The pharmaceutical composition according to claim 15 further comprising a carrier matrix or substrate.

* * * * *